US010421716B2

(12) United States Patent
MacPherson et al.

(10) Patent No.: US 10,421,716 B2
(45) Date of Patent: Sep. 24, 2019

(54) PROCESS FOR PREPARING ALPHA-CARBOXAMIDE PYRROLIDINE DERIVATIVES

(71) Applicant: Convergence Pharmaceuticals Limited, London (GB)

(72) Inventors: David MacPherson, Cambridge (GB); David Witty, Cambridge (GB); Gerard Giblin, Cambridge (GB); Michael Williams, Cambridge (GB); Donald Walker, Cambridge, MA (US); William Kiesman, Cambridge, MA (US); Tamera Mack, Cambridge, MA (US)

(73) Assignee: Convergence Pharmaceuticals Limited (GB)

( * ) Notice: Subject to any disclaimer, the term of this patent is extended or adjusted under 35 U.S.C. 154(b) by 0 days.

(21) Appl. No.: 15/539,381

(22) PCT Filed: Dec. 23, 2015

(86) PCT No.: PCT/GB2015/054140
§ 371 (c)(1),
(2) Date: Jun. 23, 2017

(87) PCT Pub. No.: WO2016/102967
PCT Pub. Date: Jun. 30, 2016

(65) Prior Publication Data
US 2017/0369437 A1 Dec. 28, 2017

(30) Foreign Application Priority Data
Dec. 23, 2014 (GB) .................................. 1423107.0

(51) Int. Cl.
*C07D 207/16* (2006.01)

(52) U.S. Cl.
CPC .................................. *C07D 207/16* (2013.01)

(58) Field of Classification Search
CPC .................................................... C07D 207/16
USPC ................................. 548/536, 537, 533, 532
See application file for complete search history.

(56) References Cited

U.S. PATENT DOCUMENTS

| 4,981,996 | A | 1/1991 | Wyss et al. |
| 5,236,957 | A | 8/1993 | Dostert et al. |
| 6,201,016 | B1 | 3/2001 | Cai et al. |
| 6,306,903 | B1 | 10/2001 | Pevarello et al. |
| 6,951,861 | B1 | 10/2005 | Alvaro et al. |
| 7,655,693 | B2 | 2/2010 | Alvaro et al. |
| 7,855,218 | B2 * | 12/2010 | Alvaro ................. C07D 207/22 514/326 |
| 2004/0097578 | A1 | 5/2004 | Jolidon et al. |
| 2004/0235752 | A1 | 11/2004 | Pitt et al. |
| 2005/0234065 | A1 | 10/2005 | Hulin et al. |
| 2008/0269208 | A1 | 10/2008 | Alvaro et al. |
| 2008/0293753 | A1 | 11/2008 | Alvaro et al. |
| 2008/0306122 | A1 | 12/2008 | Alvaro et al. |

FOREIGN PATENT DOCUMENTS

| EP | 1524265 A | 4/2005 |
| WO | WO-00/57877 A1 | 10/2000 |
| WO | WO-2004/026826 A1 | 4/2004 |
| WO | WO-04/083189 A1 | 9/2004 |
| WO | WO-04/092140 A1 | 10/2004 |
| WO | WO-04/094395 A2 | 11/2004 |
| WO | WO-05/000309 A2 | 1/2005 |
| WO | WO-2005/040108 A1 | 5/2005 |
| WO | WO-2005/110982 A2 | 11/2005 |
| WO | WO-2006/119390 A1 | 11/2006 |
| WO | WO-2006/119451 A1 | 11/2006 |
| WO | WO-2006/124865 A2 | 11/2006 |
| WO | 2007042239 A1 | 4/2007 |
| WO | 2007042240 A1 | 4/2007 |
| WO | 2007042250 A1 | 4/2007 |
| WO | WO-2007042239 A1 * | 4/2007 ........... C07D 207/22 |
| WO | WO-2008/090114 A1 | 7/2008 |
| WO | WO-2008/090115 A1 | 7/2008 |
| WO | WO-2008/090116 A1 | 7/2008 |
| WO | WO-2008/090117 A1 | 7/2008 |
| WO | WO-2008/122546 A1 | 10/2008 |
| WO | 2011015537 A1 | 2/2011 |
| WO | 2011029762 A1 | 3/2011 |
| WO | WO-2012/063252 A2 | 5/2012 |
| WO | WO-2016/102967 A1 | 6/2016 |

OTHER PUBLICATIONS

Fournie-Zaluski, M-C. et al.: "Design of orally active dual inhibitors of neutral endopeptidase angiotensin-converting enzyme with long duration action", Journal of Medicinal Chemistry, American Chemical Society, US, vol. 39, Jan. 1, 1996(Jan. 1, 1996), pp. 2594-2608.
Angelini et al., "Multistep flow procedure for the waste-minimized preparation of N-Boc-beta-Amino ketones," J Flow Chem, 41(1):40-43 (2014).
Banker et al., "Modern Pharmaceutics," 3rd edition, Marcel Dekker, New York, p. 451 and 596 (1996).
Da et al., "Highly catalytic asymmetric addition of deactivated alkyl grignard reagents to aldehydes," Organic Letters, 11(24):5578-5581 (2009).
Finelli et al., "Expanding the toolbox of asymmetric organocatalysis by continuous-flow process," Chem Commun, 51:3708-3722 (2015).
Gavezzotti et al., "Are Crystal Structures Predictable?," Accounts Chem Res, 27: 309-314 (1994).

(Continued)

Primary Examiner — Matthew P Coughlin
Assistant Examiner — Sagar Patel
(74) Attorney, Agent, or Firm — Foley Hoag LLP

(57) ABSTRACT

The invention relates to a novel process for preparing α-carboxamide pyrrolidine derivatives, in particular (2S,5R)-5-(4-((2-fluorobenzyl)oxy)phenyl)pyrrolidine-2-carboxamide, and to novel intermediates for use in said process along with processes for preparing said intermediates.

26 Claims, No Drawings

(56) References Cited

OTHER PUBLICATIONS

International Search Report and Written Opinion for International Application No. PCT/US18/54661 dated Dec. 27, 2018.
Kanemasa et al., "Stereoselective Michael Addition of the Imines of Alpha-Amino Esters in the Presence of Lithium Bromide/1,8-Diazabicyclo-[5.4.0]undec-7-ene," J Org Chem, 55(14): 4411-4417 (1990).
Lygo et al., "Co-catalyst Enhancement of Enantioselective PTC Michael Additions Involving Glycine Imines," Tetrahedron Lett, 50(26): 3363-3365 (2009).
Mancheño et al., "Chiral Copper Complexes of Phosphino Sulfenyl Ferrocenes as Efficient Catalysts for Enantioselective Formal Aza Diels—Alder Reactions of N-Sulfonyl Imines," J Am Chem Soc, 126: 456-457 (2004).
McManus et al., "Recent Developments in the Application of Oxazoline-Containing Ligands in Asymmetric Catalysis," Chem Rev, 104: 4151-4202 (2004).
Morissette et al., "High-throughput Crystallization: Polymorphs, Salts, Co-Crystals and Solvates of Pharmaceutical Solids," Adv Drug Deliver Rev, 56: 275-300 (2004).
Murray et al., "Continuous flow-processing of organometallic reagents using an advanced peristaltic pumping system and the telescoped flow synthesis of (E/Z).Tamoxifen," Organic Process Research and Development, 17:1192-1208 (2013).
Patterson et al., "An Initial Report of a New Biological Marker for Bipolar Disorder: P85 Evoked Brain Potential," Bipolar Disord, 11(6): 569-609 (2009).
Shao et al., "Phenoxyphenyl Pyridines as Novel State-Dependent, High-Potency Sodium Channel Inhibitors," J Med Chem, 47(17): 4277-4285 (2004).
Vippagunta et al., "Crystalline Solids," Adv Drug Deliv Rev, 48: 3-26 (2001).
Wolff, "Burger's Medicinal Chemistry," 5th edition, Part 1, John Wiley & Sons, p. 975-977 (1995).
Xu et al., "Asymmetric Synthesis of cis-2,5-disubsituated pyrrolidine, the core scaffold of b3-AR agonists," Organic Letters, 15(6):1342-1345 (2013).

\* cited by examiner

PROCESS FOR PREPARING ALPHA-CARBOXAMIDE PYRROLIDINE DERIVATIVES

CROSS-REFERENCE TO RELATED APPLICATIONS

This application is a 35 U.S.C. § 371 United States National Phase Application of, and claims priority to, PCT Application No. PCT/GB2015/054140, filed Dec. 23, 2015, which claims priority to Great Britain Application No. 1423107.0, filed Dec. 23, 2014. The entire contents of the aforementioned applications are incorporated herein.

FIELD OF THE INVENTION

The invention relates to a novel process for preparing α-carboxamide pyrrolidine derivatives, in particular (2S,5R)-5-(4-((2-fluorobenzyl)oxy)phenyl)pyrrolidine-2-carboxamide, and to novel intermediates for use in said process along with processes for preparing said intermediates.

BACKGROUND OF THE INVENTION (2S,5R)-5-(4-((2-fluorobenzyl)oxy)phenyl)pyrrolidine-2-carboxamide:

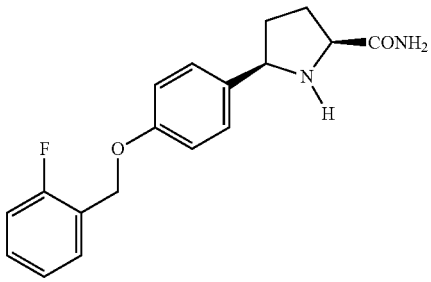 [SMILES: NC(=O)[C@@H]1CC[C@H](c2ccc(OCc3ccccc3F)cc2)N1]

is described in WO 2007/042239 as having utility in the treatment of diseases and conditions mediated by modulation of use-dependent voltage-gated sodium channels. The synthetic preparation of (2S,5R)-5-(4-((2-fluorobenzyl)oxy)phenyl)pyrrolidine-2-carboxamide is described in both WO 2007/042239 and WO 2011/029762.

However, there is a need for the development of alternative processes for the preparation of such α-carboxamide pyrrolidine derivatives, which are capable of practical application to large scale manufacture.

SUMMARY OF THE INVENTION

According to a first aspect of the invention, there is provided a compound of formula (I):

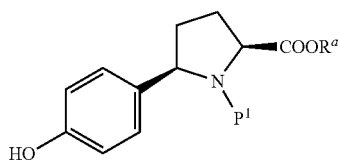

wherein $R^a$ represents a $C_{1-3}$ alkyl group, such as methyl or ethyl, in particular methyl, and $P^1$ represents a suitable protecting group.

According to a further aspect of the invention, there is provided a process for preparing a compound of formula (I) which comprises:

(i) preparing a compound of formula (II) by reacting a compound of formula (III) with a compound of formula (IV):

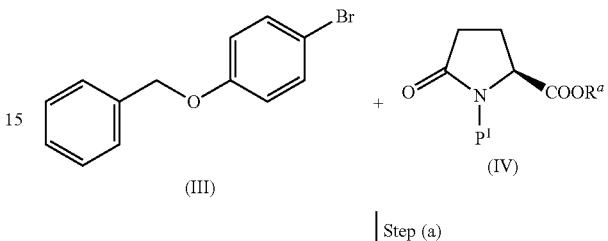

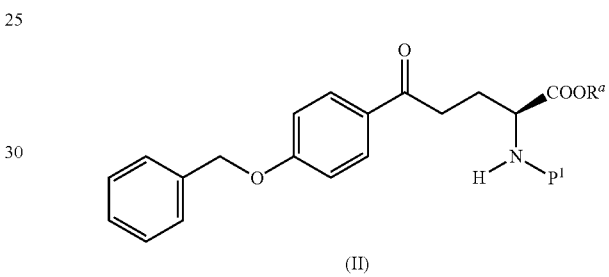

wherein $P^1$ and $R^a$ are as defined herein; followed by (ii) preparing a compound of formula (V) from a compound of formula (II):

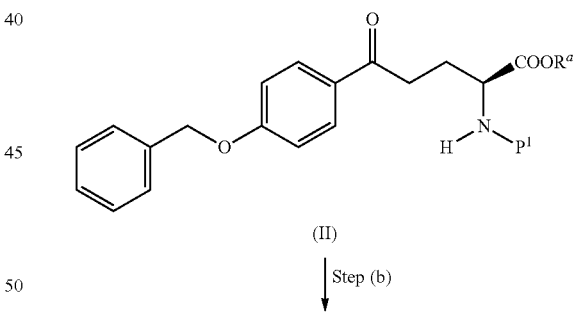

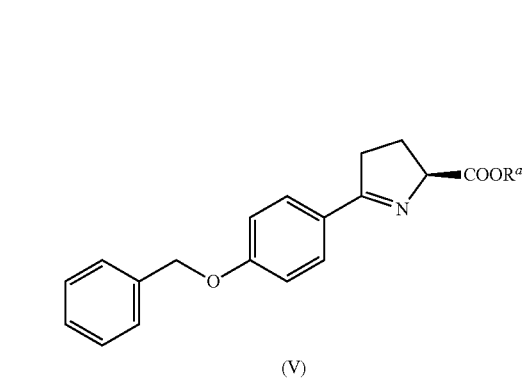

wherein $R^a$ and $P^1$ are as defined herein; followed by (iii) preparing a compound of formula (I) from a compound of formula (V):

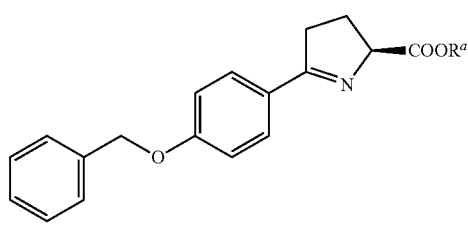

(V)

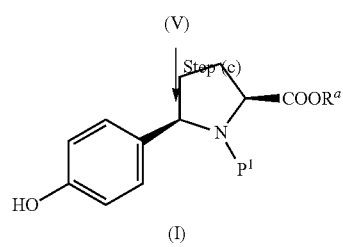

(I)

wherein $R^a$ and $P^1$ are as defined herein.

According to a further aspect of the invention, there is provided a process for preparing a compound of formula (VI)$^a$ which comprises:

(i) preparing a compound of formula (II) by reacting a compound of formula (III) with a compound of formula (IV):

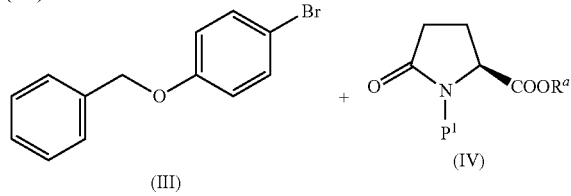

(III)   (IV)

| Step (a)

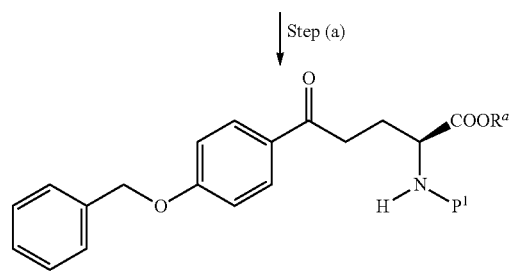

(II)

wherein $R^a$ and $P^1$ are as defined herein; followed by (ii) preparing a compound of formula (V) from a compound of formula (II):

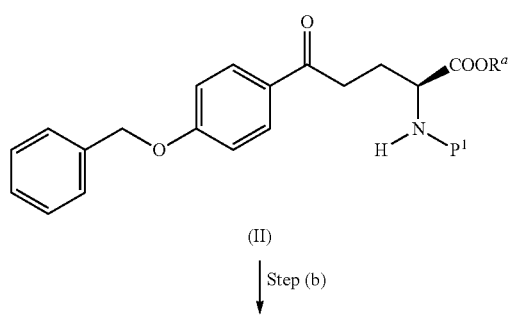

(II)

| Step (b)

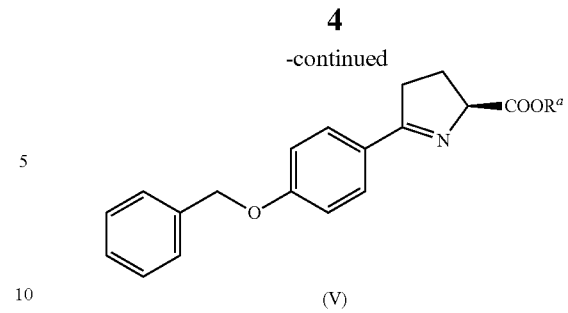

(V)

wherein $R^a$ and $P^1$ are as defined herein; followed by (iii) preparing a compound of formula (I) from a compound of formula (V):

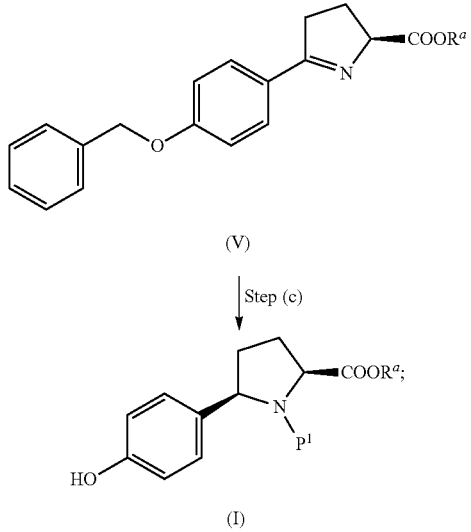

(V)

| Step (c)

(I)

wherein $R^a$ and $P^1$ are as defined herein; followed by (iv) preparing a compound of formula (VII) from a compound of formula (I) by reacting the compound of formula (I) with a compound of formula (VIII):

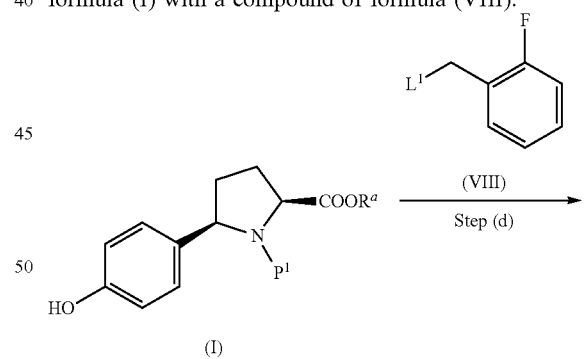

(I)

(VIII)
Step (d)

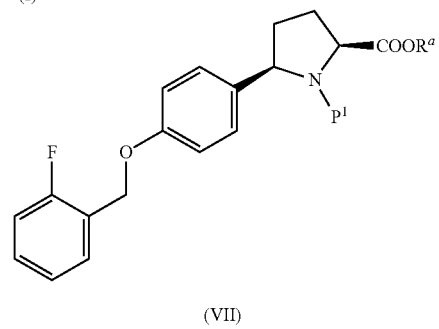

(VII)

wherein R<sup>a</sup> and P¹ are as defined herein and L¹ represents a suitable leaving group; followed by (v) preparing a compound of formula (IX) from a compound of formula (VII) by removal of the P¹ group under suitable deprotection conditions:

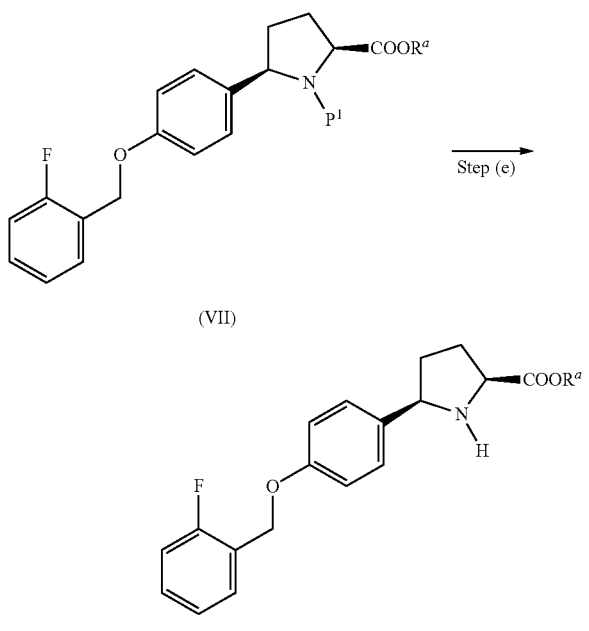

(VII)

↓ Step (e)

(IX)

wherein R<sup>a</sup> and P¹ are as defined herein; followed by (vi) preparing a compound of formula (VI)<sup>a</sup> from a compound of formula (IX):

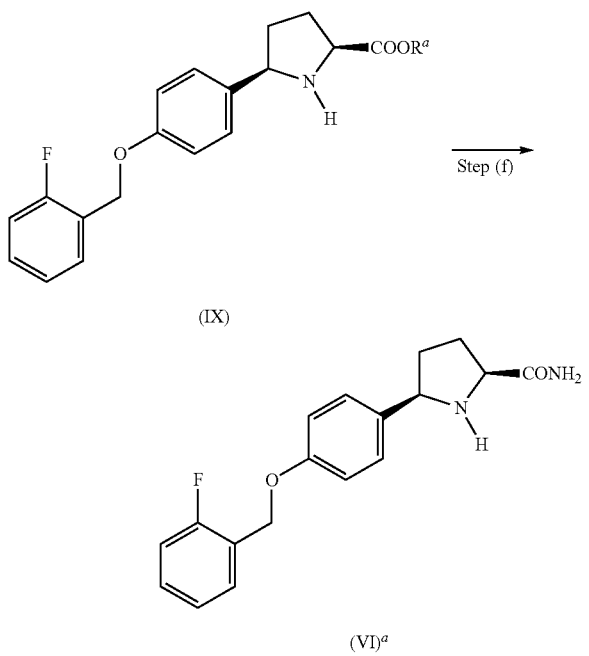

(IX)

↓ Step (f)

(VI)<sup>a</sup> wherein R<sup>a</sup> is as defined herein.

According to a further aspect of the invention, there is provided a compound obtainable by a process as defined herein.

DETAILED DESCRIPTION OF THE INVENTION

According to a first aspect of the invention, there is provided a compound of formula (I):

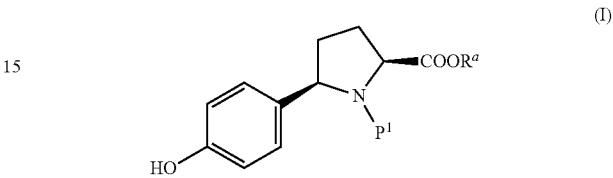

(I)

wherein R<sup>a</sup> represents a $C_{1-3}$ alkyl group, such as methyl or ethyl, in particular methyl, and P¹ represents a suitable protecting group.

It will be appreciated that P¹ represents any suitable amine protecting group. Examples of suitable amine protecting groups include: tert-butyloxycarbonyl (BOC); 9-fluorenyl-methyloxycarbonyl (FMOC); acetyl (Ac); benzoyl (Bz); carbamate; p-methoxyphenyl (PMP); tosyl (Ts); a sulfonamide selected from Nosyl and Nps; and trifluoroacetyl.

In one embodiment, P¹ represents tert-butyloxycarbonyl (BOC). Thus, in a further embodiment, the compound of formula (I) is a compound of formula (I)<sup>a</sup>:

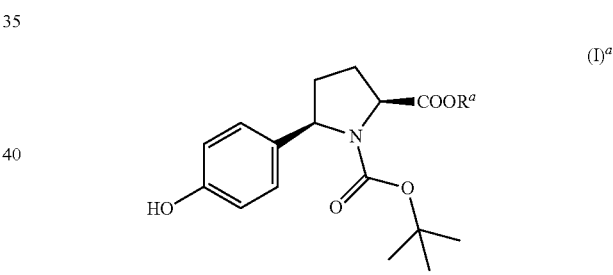

(I)<sup>a</sup> wherein R<sup>a</sup> is as defined herein.

In one embodiment, R<sup>a</sup> represents methyl or ethyl. In a further embodiment, R<sup>a</sup> represents methyl. Thus, in a further embodiment, the compound of formula (I) is a compound of formula (I)<sup>b</sup>;

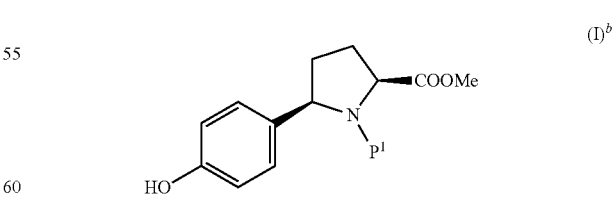

(I)<sup>b</sup> wherein P¹ is as defined herein.

In one embodiment, R<sup>a</sup> represents methyl and P¹ represents tert-butyloxycarbonyl (BOC). Thus, in a further embodiment, the compound of formula (I) is a compound of formula (I)<sup>c</sup>:

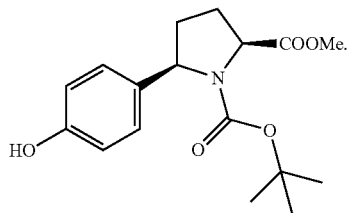

(I)ᶜ

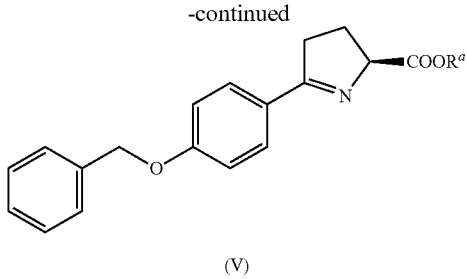

(V)

According to a further aspect of the invention, there is provided a process for preparing a compound of formula (I) which comprises:

(i) preparing a compound of formula (II) by reacting a compound of formula (III) with a compound of formula (IV):

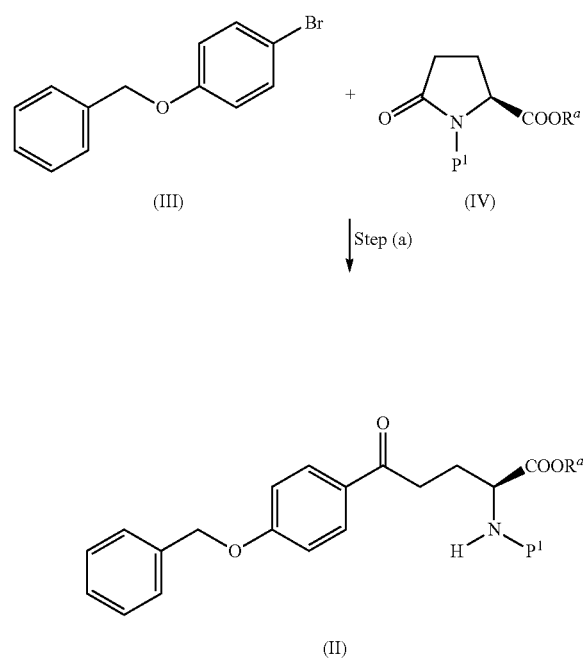

wherein $P^1$ and $R^a$ are as defined herein; followed by (ii) preparing a compound of formula (V) from a compound of formula (II):

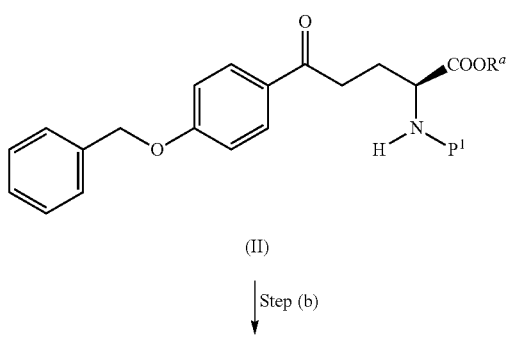

wherein $R^a$ and $P^1$ are as defined herein; followed by (iii) preparing a compound of formula (I) from a compound of formula (V):

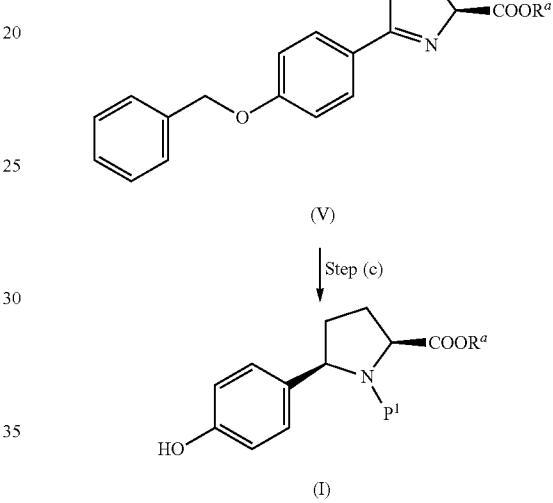

wherein $R^a$ and $P^1$ are as defined herein.

The Grignard reaction which prepares the compound of formula (II) by reacting a compound of formula (III) with a compound of formula (IV) provides significant advantages over previously described procedures for preparing α-carboxamide pyrrolidine derivatives. For example, the previously described procedures contain a 2-fluoro group which remains in situ throughout the entire procedure. The incorporation of said 2-fluoro group in step (a) unexpectedly results in benzynyl derived impurities, however, incorporation of the 2-fluoro group in step (d) solves this problem concerning the presence of these impurities. This resulting improvement in impurity profile results in advanced intermediates and final compounds of improved colour which has a beneficial effect regarding formulating the final product for pharmaceutical use. Furthermore, the yield obtained in step (a) is improved when compared with previously described procedures for preparing α-carboxamide pyrrolidine derivatives.

It is believed that preparation of the compound of formula (I) from the compound of formula (V) involves incorporation of a second chiral centre via stereoselective reduction of the imine to form an amine which is then protected by addition of a protecting group. The benzyl group is also removed during this process. The preparation of the compound of formula (I) in step (c) has surprisingly been found to provide a number of key advantages, for example, the resultant compound of formula (I) has been found to have a greater level of diastereoisomer purity when compared with previously described procedures for preparing α-carboxamide pyrrolidine derivatives. For example, very low levels (i.e. <1%) of the anti-isomer in the product of compound of formula (I) were observed compared with 5-10% in previously described procedures for preparing α-carboxamide pyrrolidine derivatives. In addition, the solid crystalline nature of the compound of formula (I) facilitates further reduction in the quantity of the anti-isomer. Furthermore, the addition of the P¹ protecting group greatly assists in isolation of the intermediate compound of formula (I) and also ensures that the compound of formula (VIII) in step (d) is added to the oxygen atom and not the protected nitrogen. Therefore, the compound of formula (I) represents a novel and valuable intermediate in the preparation of α-carboxamide pyrrolidine derivatives, such as the compound of formula (VI) and (VI)$^a$.

According to a further aspect of the invention, there is provided a process for preparing a compound of formula (I) which comprises:

(i) preparing a compound of formula (I) from a compound of formula (V):

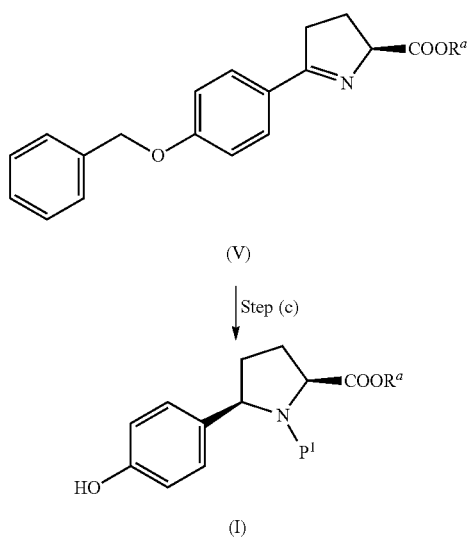

wherein R$^a$ and P¹ are as defined herein.

As mentioned hereinbefore, the compound of formula (I) represents a valuable intermediate in the preparation of α-carboxamide pyrrolidine derivatives, such as the compound of formula (VI), thus, according to a further aspect of the invention, there is provided the use of a compound of formula (I) as defined herein or obtainable by the process as defined herein, as an intermediate in the preparation of a compound of formula (VI):

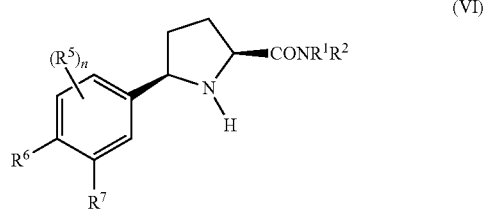

wherein

R¹ and R² are independently hydrogen, $C_{1-6}$ alkyl or $C_{3-6}$ cycloalkyl$C_{1-6}$ alkyl; or such R¹ and R², together with the nitrogen to which they are attached, may form an unsubstituted 3-, 4-, 5- or 6-membered saturated ring;

n is 0, 1 or 2, wherein when present each R⁵ is independently selected from the list consisting of $C_{1-3}$ alkyl, halogen, cyano, halo$C_{1-3}$ alkyl, hydroxy, $C_{1-3}$ alkoxy and $C_{1-3}$ haloalkoxy;

either R⁶ or R⁷ is —O—R⁸, —OCHR⁹R⁸, —NCH₂R⁸ or —(CH₂)₂R⁸ wherein the other R⁶ or R⁷ is hydrogen or R⁵;

and wherein R⁸ is a phenyl ring or wherein the phenyl ring is optionally substituted by one or more groups independently selected from the list consisting of $C_{1-3}$ alkyl, halogen, cyano, halo$C_{1-3}$ alkyl, hydroxy, $C_{1-3}$ alkoxy and $C_{1-3}$ haloalkoxy; and R⁹ is hydrogen or $C_{1-3}$ alkyl.

In one embodiment, the compound of formula (VI) is a compound wherein:

R¹ and R² are independently hydrogen, $C_{1-6}$ alkyl or $C_{3-6}$ cycloalkyl$C_{1-6}$ alkyl; or such R¹ and R², together with the nitrogen to which they are attached, may form an unsubstituted 3-, 4-, 5- or 6-membered saturated ring;

n is 0;

R⁶ is —O—R⁸ or —OCHR⁹R⁸;

R⁷ is hydrogen;

R⁸ is a phenyl ring optionally substituted by one or more groups independently selected from the list consisting of $C_{1-3}$ alkyl, halogen, cyano, halo$C_{1-3}$ alkyl, hydroxy, $C_{1-3}$ alkoxy and $C_{1-3}$ haloalkoxy; and R⁹ is hydrogen or $C_{1-3}$ alkyl.

As mentioned hereinbefore, the compound of formula (I) represents a valuable intermediate in the preparation of the compound of formula (VI)$^a$, thus, in a further embodiment, the compound of formula (VI) is a compound of formula (VI)$^a$:

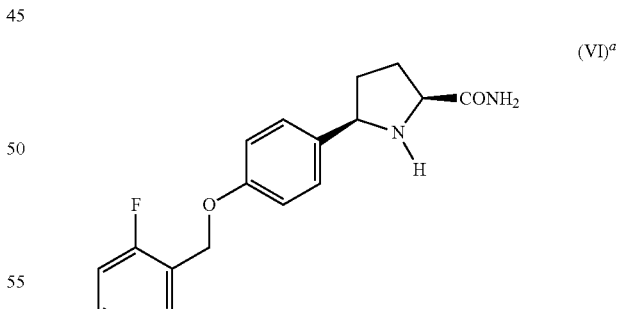

i.e. (2S,5R)-5-(4-((2-fluorobenzyl)oxy)phenyl)pyrrolidine-2-carboxamide.

According to a further aspect of the invention, there is provided a process for preparing a compound of formula (VI)$^a$ which comprises:

(i) preparing a compound of formula (VII) from a compound of formula (I) by reacting the compound of formula (I) with a compound of formula (VIII):

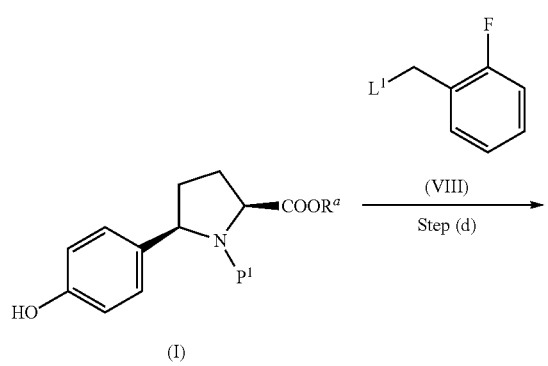

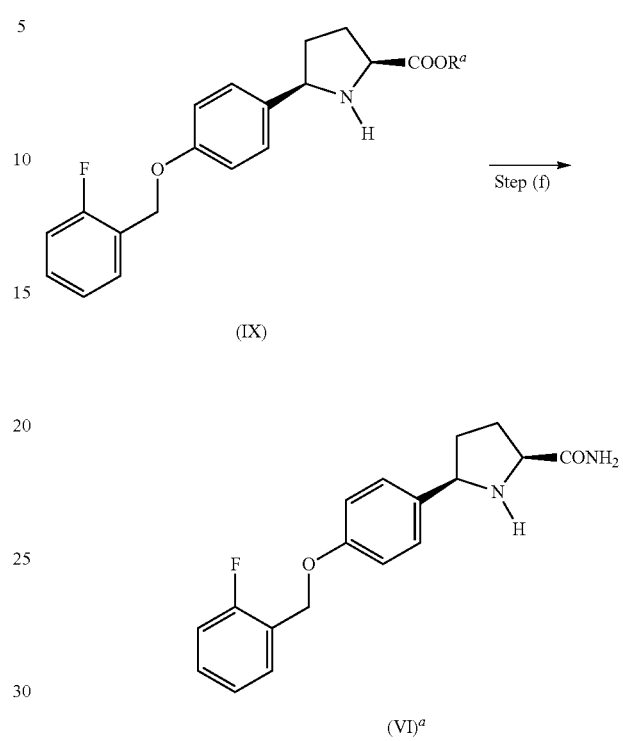

(iii) preparing a compound of formula (VI)$^a$ from a compound of formula (IX):

wherein R$^a$ is as defined herein.

According to a further aspect of the invention, there is provided a process for preparing a compound of formula (VI)$^a$ which comprises:

(i) preparing a compound of formula (II) by reacting a compound of formula (III) with a compound of formula (IV):

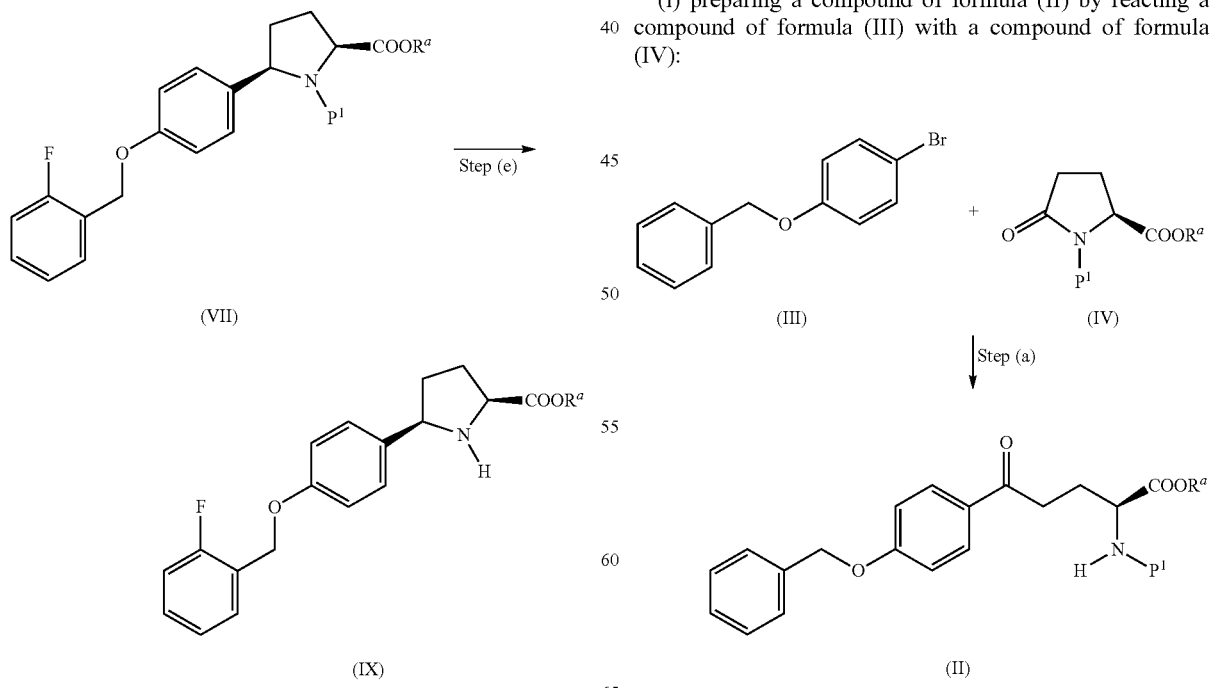

wherein R$^a$ and P$^1$ are as defined herein and L$^1$ represents a suitable leaving group; followed by (ii) preparing a compound of formula (IX) from a compound of formula (VII) by removal of the P$^1$ group under suitable deprotection conditions:

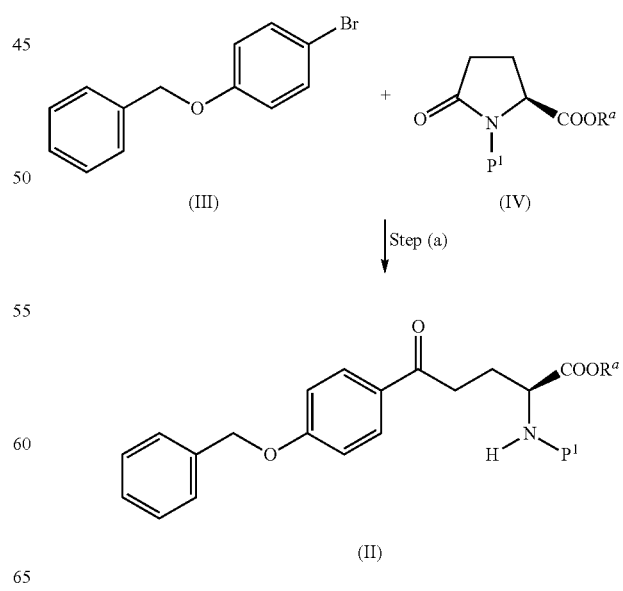

wherein R$^a$ and P$^1$ are as defined herein; followed by wherein R$^a$ and P$^1$ are as defined herein; followed by (ii) preparing a compound of formula (V) from a compound of formula (II):

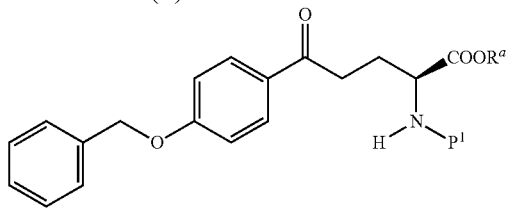

(II)

Step (b)

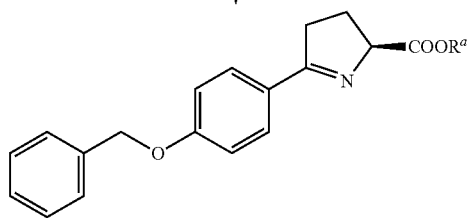

(V)

wherein $R^a$ and $P^1$ are as defined herein; followed by (iii) preparing a compound of formula (I) from a compound of formula (V):

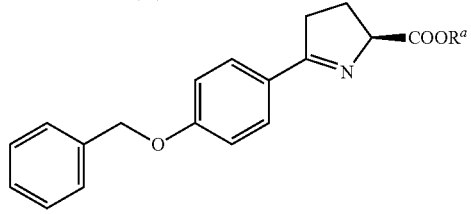

(V)

Step (c)

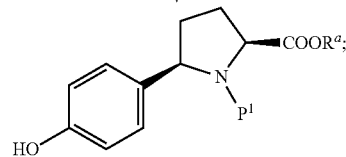

(I)

wherein $R^a$ and $P^1$ are as defined herein; followed by (iv) preparing a compound of formula (VII) from a compound of formula (I) by reacting the compound of formula (I) with a compound of formula (VIII):

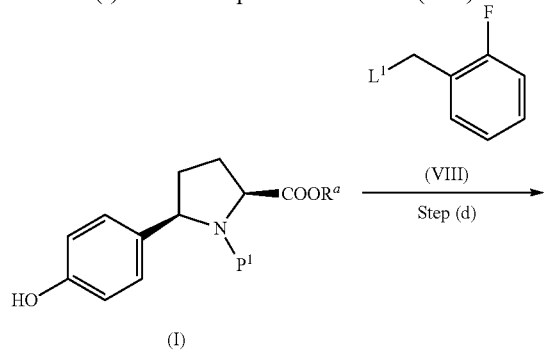

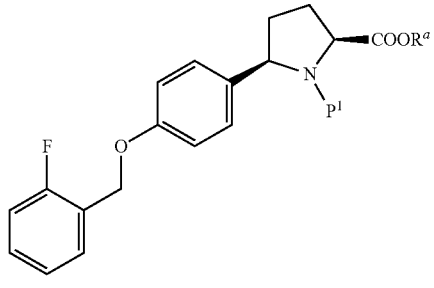

(VII)

wherein $R^a$ and $P^1$ are as defined herein and $L^1$ represents a suitable leaving group; followed by (v) preparing a compound of formula (IX) from a compound of formula (VII) by removal of the $P^1$ group under suitable deprotection conditions:

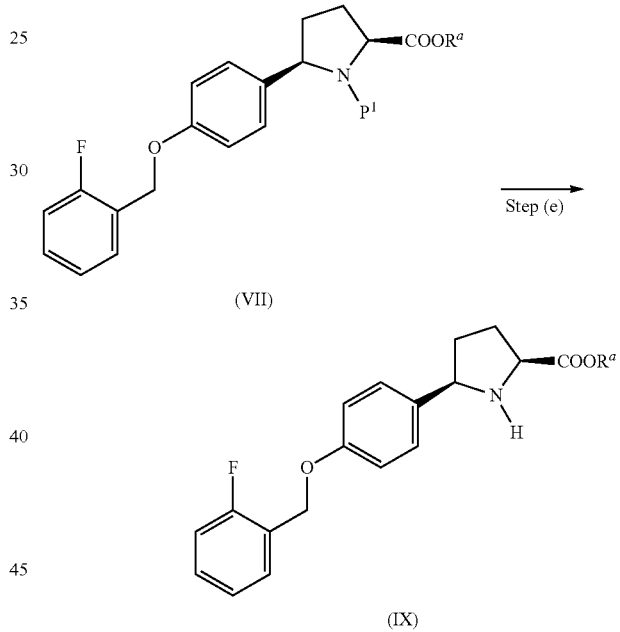

wherein $R^a$ and $P^1$ are as defined herein; followed by (vi) preparing a compound of formula (VI)$^a$ from a compound of formula (IX):

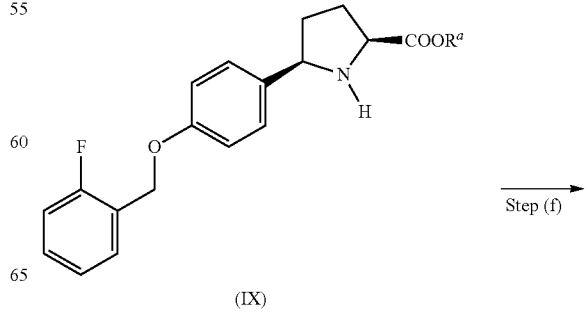

(IX)

Step (f)

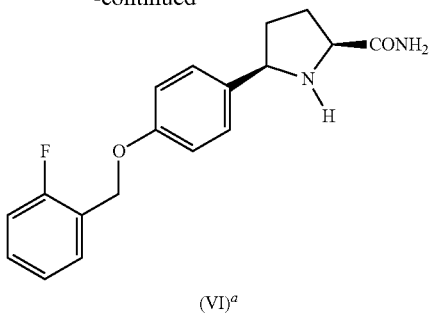

wherein $R^a$ is as defined herein.

In one embodiment of any of the aforementioned processes, step (a) comprises the use of magnesium, such as magnesium under nitrogen to form a Grignard reagent, and a suitable solvent, such as tetrahydrofuran (THF). The full experimental procedure for step (a) as referred to herein is provided as Description 1.

In one embodiment of any of the aforementioned processes, step (b) comprises the use of a suitable solvent, such as dichloromethane (DCM), acetonitrile or toluene, in particular toluene, and a suitable acid, such as trifluoroacetic acid (TFA) or methanesulfonic acid. In a further embodiment of any of the aforementioned processes, step (b) comprises the use of trifluoroacetic acid in toluene or methanesulfonic acid in acetonitrile. Under certain circumstances, when methanesulfonic acid is used as the acid in step (b), an intermediate may be obtained where $P^1$ represents hydrogen prior to cyclisation, i.e. a compound of formula $(II)^a$:

$(II)^a$ wherein $R^a$ is as defined hereinbefore.

In a further embodiment of any of the aforementioned processes, step (b) comprises the use of a suitable solvent, such as dichloromethane (DCM) and a suitable acid, such as trifluoroacetic acid (TFA).

The full experimental procedure for step (b) as referred to herein is provided as Description 2.

In one embodiment of any of the aforementioned processes, when $P^1$ represents tert-butyloxycarbonyl (BOC), step (c) comprises the use of $Boc_2O$ in a suitable solvent, such as methanol and in the presence of a suitable catalyst, such as Pd—C, in particular 5% or 10% Pd—C. Step (c) is typically performed under a hydrogen atmosphere. The full experimental procedure for step (c) as referred to herein is provided as Description 3. Thus, alternative reagents for step (c) may also include $Pd(OH)_2$ and N-(tert-butoxycarbonyloxy)succinimide typically also under a hydrogen atmosphere.

In one embodiment of any of the aforementioned processes, $L^1$ represents a halogen atom, such as a bromine atom.

In one embodiment of any of the aforementioned processes, step (d) comprises the use of a suitable base, such as potassium carbonate and a suitable solvent, such as acetone. This step may optionally be performed in the presence of a phase transfer catalyst, such as tetra n-butyl ammonium bromide in the presence of a suitable solvent, such as ethyl acetate. The full experimental procedure for step (d) as referred to herein is provided as Description 4.

It will be appreciated by the skilled person that the deprotection reaction referred to in step (e) will comprise any suitable conditions for removing the $P^1$ protecting group. For example: tert-Butyloxycarbonyl (BOC) may be removed by concentrated strong acid (such as HCl, $CF_3COOH$, 80-85% phosphoric acid or a sulfonic acid such as para-toluenesulfonic acid, in particular HCl, $CF_3COOH$ or 80-85% phosphoric acid), or by heating to >80° C.; 9-fluorenylmethyloxycarbonyl (FMOC) may be removed by a suitable base, such as piperidine; acetyl (Ac) may be removed by treatment with a base, most often, with aqueous or gaseous ammonia or methylamine; benzoyl (Bz) may be removed by treatment with a base, most often with aqueous or gaseous ammonia or methylamine; carbamate may be removed by acid and mild heating; p-methoxyphenyl (PMP) may be removed by ammonium cerium(IV) nitrate (CAN); tosyl (Ts) may be removed by concentrated acid (HBr, $H_2SO_4$) and strong reducing agents (sodium in liquid ammonia or sodium naphthalenide); selected sulfonamides (such as Nosyl and Nps) may be removed by samarium iodide or tributyltin hydride and trifluoroacetyl may be removed with ammonia or other suitable base. The use of ammonia for removal of the trifluoroacetyl group in step (e) provides the advantage of allowing steps (e) and (f) to be performed in a single stage.

Thus, in one embodiment of any of the aforementioned processes, when $P^1$ represents tert-butyloxycarbonyl (BOC), step (e) comprises the use of a strong acid, such as hydrochloric acid in a suitable solvent, such as dioxan. The full experimental procedure for step (e) as referred to herein is provided as Description 5.

In alternative embodiment, when $P^1$ represents tert-butyloxycarbonyl (BOC), step (e) comprises the use of a strong acid, such as phosphoric acid, in particular 80-85% phosphoric acid in a suitable solvent, such as MTBE.

In alternative embodiment, when $P^1$ represents tert-butyloxycarbonyl (BOC), step (e) comprises the use of methanesulfonic, benzenesulfonic or p-toluenesulfonic acid.

In alternative embodiment, when $P^1$ represents tert-butyloxycarbonyl (BOC), step (e) comprises the use of p-toluenesulfonic acid in a suitable solvent, such as methanol. The experimental procedure for step (e) comprising the use of p-toluenesulfonic acid is provided as Description 5a.

In one embodiment of any of the aforementioned processes, step (f) comprises the use of ammonia in a suitable solvent, such as methanol.

The full experimental procedure for step (f) as referred to herein is provided as Description 6.

In one embodiment of any of the aforementioned processes, said process additionally comprises the step of preparing a salt of a compound of formula $(VI)^a$ by treating the compound of formula $(VI)^a$ with a suitable acid.

In a further embodiment, the salt of a compound of formula $(VI)^a$ is the hydrochloride salt and the suitable acid comprises strong hydrochloric acid, such as 4M hydrochloric acid in a suitable solvent, such as dioxan. Full experimental procedure for one such salt preparation referred to herein is provided as Example 1.

In an alternative embodiment, the salt of a compound of formula (VI)$^a$ is the hydrochloride salt and the suitable acid comprises strong hydrochloric acid, such as hydrochloric acid in a suitable solvent, such as ethanol. Full experimental procedure for one such salt preparation referred to herein is provided as Example 1 (Alternative Procedure) and (Large Scale Plant Manufacture).

As referred to hereinbefore, the novel intermediate of compound of formula (I) imparts a beneficial property with respect to diastereoisomer purity upon the compounds which are prepared from said intermediate, thus, according to a further aspect of the invention, there is provided a compound obtainable by a process as defined herein.

It will be appreciated that the intermediate compound of formula (I) may also find utility in the preparation of related α-carboxamide pyrrolidine derivatives, such as those described in WO 2007/042240. Thus, according to a further aspect of the invention there is provided the use of a compound of formula (I) as defined herein or obtainable by the process as defined herein, as an intermediate in the preparation of a compound of formula (X):

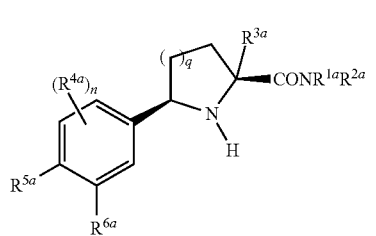

(X)

wherein
R$^{1a}$ and R$^{2a}$ are independently hydrogen, C$_{1-6}$ alkyl or C$_{3-6}$ cycloalkylC$_{1-6}$ alkyl; or such R$^{1a}$ and R$^{2a}$, together with the nitrogen to which they are attached, may form an unsubstituted 3-, 4-, 5- or 6-membered saturated ring;
R$^{3a}$ is C$_{1-6}$ alkyl, C$_{1-6}$ haloalkyl, C$_{1-3}$ alkenyl, C$_{1-3}$ alkoxyC$_{1-3}$ alkyl, C$_{1-3}$ haloalkoxyC$_{1-3}$ alkyl or (CH$_2$)$_t$OH;
or such R$^{1a}$ and R$^{3a}$, together with the interconnecting atoms, form a saturated or unsaturated 5- to 7-membered ring, with the proviso that there is only one heteroatom in the ring, which must be nitrogen;
n is 0, 1 or 2, wherein when present each R$^{4a}$ is independently selected from the list consisting of C$_{1-3}$ alkyl, halogen, cyano, haloC$_{1-3}$ alkyl, hydroxy, C$_{1-3}$ alkoxy and C$_{1-3}$ haloalkoxy,
q is 1 or 2;
t is 1 or 2;
either R$^{5a}$ or R$^{6a}$ is —O—R$^{7a}$ or —OCH$_2$R$^{7a}$, wherein the other R$^{5a}$ or R$^{6a}$ is hydrogen or R$^{4a}$; and wherein R$^{7a}$ is either a phenyl ring or a 5- or 6-membered aromatic heterocyclic ring (independently containing one or more nitrogen, sulphur or oxygen atoms) wherein either the phenyl ring or the heterocyclic ring is optionally substituted by one or more groups independently selected from the list consisting of C$_{1-3}$ alkyl, halogen, cyano, haloC$_{1-3}$ alkyl, hydroxy, C$_{1-3}$ alkoxy and C$_{1-3}$ haloalkoxy.

In one embodiment, the compound of formula (X) is a compound wherein:
R$^{1a}$ and R$^{2a}$ are independently hydrogen, C$_{1-6}$ alkyl or C$_{3-6}$ cycloalkylC$_{1-6}$ alkyl; or such R$^{1a}$ and R$^{2a}$, together with the nitrogen to which they are attached, may form an unsubstituted 3-, 4-, 5- or 6-membered saturated ring;
R$^{3a}$ is C$_{1-6}$ alkyl, C$_{1-6}$ haloalkyl, C$_{1-3}$ alkenyl, C$_{1-3}$ alkoxyC$_{1-3}$ alkyl, C$_{1-3}$ haloalkoxyC$_{1-3}$ alkyl or (CH$_2$)$_t$OH;
or such R$^{1a}$ and R$^{3a}$, together with the interconnecting atoms, form a saturated or unsaturated 5- to 7-membered ring, with the proviso that there is only one heteroatom in the ring, which must be nitrogen;
n is 0;
q is 1 or 2;
t is 1 or 2;
R$^{5a}$ is —O—R$^{7a}$ or —OCH$_2$R$^{7a}$;
R$^{6a}$ is hydrogen;
R$^{7a}$ is either a phenyl ring or a 5- or 6-membered aromatic heterocyclic ring (independently containing one or more nitrogen, sulphur or oxygen atoms) wherein either the phenyl ring or the heterocyclic ring is optionally substituted by one or more groups independently selected from the list consisting of C$_{1-3}$ alkyl, halogen, cyano, haloC$_{1-3}$ alkyl, hydroxy, C$_{1-3}$ alkoxy and C$_{1-3}$ haloalkoxy.

In a further embodiment, the compound of formula (X) is a compound of formula (X)$^a$:

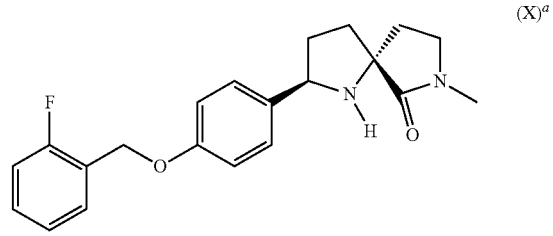 [SMILES: CN1CC[C@]2(CC[C@H](c3ccc(OCc4ccccc4F)cc3)N2)C1=O]

(X)$^a$ i.e. (2R,5R)-2-(4-{[(2-fluorophenyl)methyl]oxy}phenyl)-7-methyl-1,7-diazaspiro[4.4]nonan-6-one or a pharmaceutically acceptable salt thereof.

It will be apparent to the skilled person that the compound of formula (X)$^a$ may be prepared from a compound of formula (I) via step (d) referred to herein which prepares a compound of formula (VII). Description 4 describes the preparation of a compound of formula (VII) where P$^1$ represents BOC. The compound prepared in Description 4 herein is identical to the compound prepared in Description 34 of WO 2007/042240, therefore, WO 2007/042240 provides the skilled person with guidance of how the compound of formula (X)$^a$ may be prepared from Description 4 described herein.

In an alternative embodiment, the compound of formula (X) is a compound of formula (X)$^b$:

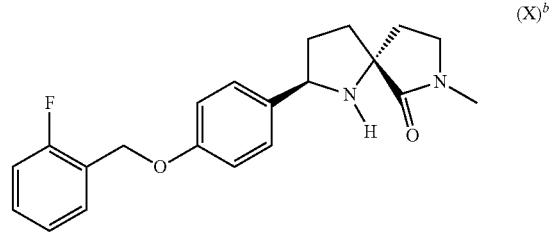

(X)$^b$

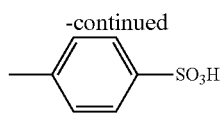

i.e. (2R,5R)-2-(4-{[(2-fluorophenyl)methyl]oxy}phenyl)-7-methy-1,7-diazaspiro[4.4]nonan-6-one tosylate.

In an alternative embodiment, the compound of formula (X) is a compound of formula (X)$^c$:

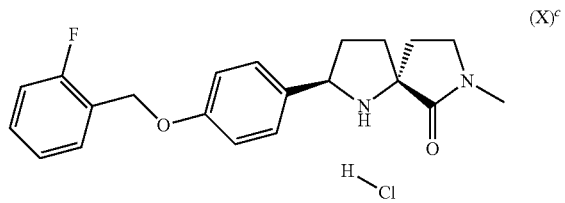 [SMILES: CN1CC[C@]2(CC[C@H](c3ccc(OCc4ccccc4F)cc3)N2)C1=O ; Cl]

i.e. (2R,5R)-2-(4-{[(2-fluorophenyl)methyl]oxy}phenyl)-7-methyl-1,7-diazaspiro[4.4]nonan-6-one hydrochloride.

EXAMPLES

The invention is illustrated by the Examples described below.

In the procedures that follow, after each starting material, reference to a Description or Example by number is typically provided. This is provided merely for assistance to the skilled chemist. The starting material may not necessarily have been prepared from the batch referred to.

Where reference is made to the use of a "similar" procedure, as will be appreciated by those skilled in the art, such a procedure may involve minor variation, for example reaction temperature, reagent/solvent amount, reaction time, work-up conditions or chromatographic purification conditions.

Proton Magnetic Resonance (NMR) spectra are typically recorded on Bruker instruments at 300, 400 or 500 MHz. Chemical shifts are reported in ppm (δ) using the residual solvent line as internal standard. Splitting patterns are designated as s, singlet; d, doublet; t, triplet; q, quartet; m, multiplet; br, broad. The NMR spectra were typically recorded at a temperature of 25° C.

LC-MS Data (LC-MS) is typically generated on an Waters ZQ Mass Spectrometer, operating in switched ES+ and ES− ionization modes coupled to an Agilent 1100 Series HPLC system with in line Aglient 1100 UV-DAD and Sedere SEDEX 75 ELSD Detection. Instrument control and data acquisition is mediated through the Waters MassLynx-OpenLynx software suite. Separation was performed on a Waters SunFire C18 (30×4.6 mm, 3.5 μm) column Flow Rate: 3.0 mL/min. column temperature 30° C. Injection Volume: 5.0 μL. Mobile phase [A]: 3:97:0.05 (v/v/v) Acetonitrile:Water:Formic Acid. Mobile Phase [B]: 97:3:0.05 (v/v/v) Acetonitrile:Water:Formic Acid. Gradient: 97% [A] 3% [B] for 0.1 min. Ramp to 3% [A] 97% [B] at 4.0 min. Hold at 97% [B] to 5 min. Return to 97% [A] at 6 min. Detector parameters: UV-DAD: Range 190 to 450 nm, Interval 2 nm, Threshold 0.1 mAU. ELSD: Temperature 40° C., Range 8. Mass Spectrometer: ES−: Mass Range 125 to 625 in 0.50 sec. Interscan delay 0.25 sec. Capillary 4.0 kV. ES−: Mass Range 125 to 625 in 0.50 sec. Interscan delay 0.25 sec. Capillary 3.0 kV.

In the mass spectra only one peak in the molecular ion cluster is usually reported.

The following abbreviations are used herein:
Boc tertButyloxycarbonyl
Boc$_2$O Di-tert-butyl dicarbonate
CHCl$_3$ Chloroform
DCM Dichloromethane
DMSO Dimethylsulfoxide
EtOAc Ethyl Acetate
HCl Hydrochloric Acid
K$_2$CO$_3$ Potassium carbonate
LC-MS Liquid chromatography-Mass spectrometry
MTBE Methyl t-butyl ether
MeCN Acetonitrile
MeOH Methanol
Na$_2$CO$_3$ Sodium carbonate
NMR Nuclear Magnetic Resonance
NaOH Sodium hydroxide
Na$_2$SO$_4$ Sodium sulfate
TFA Trifluoroacetic acid
THF Tetrahydrofuran Description 1: (S)-Methyl 5-(4-(benzyloxyphenyl)-2-((tert-butoxycarbonyl)amino)-5-oxopentanoate (D1)

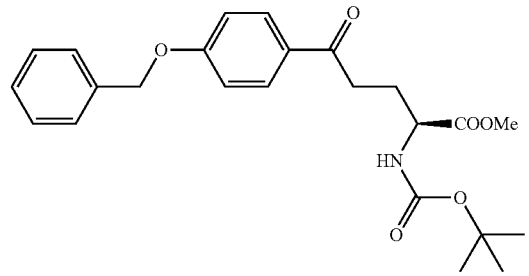 [SMILES: COC(=O)[C@H](CCC(=O)c1ccc(OCc2ccccc2)cc1)NC(=O)OC(C)(C)C]

5 ml of a solution of 1-benzyloxy-4-bromo-benzene (43.267 g, 164.43 mmol) in THF (200 ml) was added to magnesium (4.8 g, 197.32 mmol) under nitrogen. A crystal of iodine was added and the mixture was stirred and heated until the iodine decolorized (reflux) and then the remainder of the solution was added dropwise over 45 minutes whilst maintaining reflux. After completion of the addition, the mixture was refluxed for 1 hr.

The mixture was allowed to cool, transferred via syringe to a dropping funnel and was then added dropwise to a solution of (S)-1-tert-butyl-2-methyl-5-oxopyrrolidine-1,2-dicarboxylate (20 g, 82.22 mmol) in THF (200 ml) at −70° C. under nitrogen at such a rate as to keep the temperature below −65° C. (addition took about 45 minutes). After completion of the addition, the mixture was stirred in a dry/ice acetone bath for a further 90 minutes (temp −75° C.).

Isopropyl alcohol (40 ml) was added dropwise whilst maintaining the temperature below −60° C., followed by a mixture of saturated aq. NH$_4$Cl (80 ml) and NaCl (40 ml) solutions also added dropwise at such a rate to keep the temperature below −60° C. After completion of the addition, the mixture was allowed to warm to room temperature and ethyl acetate/water (400 ml/150 ml) were added and the product was extracted into ethyl acetate (initial 400 ml and then 200 ml×2) and the combined organic extracts were washed with brine (200 ml), dried (Na$_2$SO$_4$) and evaporated.

The product was stirred for 90 minutes in heptane (200 ml) and the resulting solid was collected by filtration and washed with heptane (2×40 ml) and then dried under vacuum to give product as a beige solid (D1, Yield 100% wt. recovery)

LC-MS see MH$^+$=428 (C$_{24}$H$_{29}$NO$_6$ requires 427)

NMR (1H, CDCl$_3$, ppm): 1.52 (9H, s), 2.10 (1H, m), 2.30 (1H, m), 2.95-3.15 (2H, m), 3.76 (3H, s), 4.40 (1H, m), 5.15 (2H, s), 5.18 (1H, br s), 7.03 (2H, d, J=9 Hz), 7.30-7.50 (5H, m), 7.95 (2H, d, J=9 Hz).

Description 1: (S)-Methyl 5-(4-(benzyloxyphenyl)-2-((tert-butoxycarbonyl)amino)-5-oxopentanoate (D1) (Large Scale Plant Manufacture)

Magnesium turnings (0.296 kg) and iodine (36 g) were charged into a reactor under a nitrogen atmosphere and the mixture was heated at 105° C. for 2-3 hours. The mixture was cooled to 30° C. and THF (18 L) and iodine (36 g) were added and the mixture was heated to 65° C. In another vessel, benzyloxy-4-bromobenzene (17 kg) was dissolved in THF (45 L) and stirred at room temperature. Approx 5% of this solution was added over 30-60 minutes to the refluxing suspension of magnesium above and 1,2-dibromoethane (36 ml) was added to initiate Grignard formation. The remaining solution of benzyloxy-4-bromobenzene was added under nitrogen over a period of 4-5 hours. After completion of the addition, the mixture was refluxed under nitrogen until the starting bromide had reacted (usually 60-120 minutes) and then the mixture was cooled to 30° C.

A separate vessel was charged with N-boo-L-pyroglutamic acid methyl ester (9 kg) and THF (5 volumes) under nitrogen and the mixture was stirred and cooled to −65° C. The Grignard solution prepared above was added slowly whilst maintaining the temperature at −65±5° C. (approx. 150 minutes) and after completion of the addition, the reaction was maintained at the same temperature for 60-120 minutes. Isopropanol (9 L) was added to the reaction mass at −65±5° C. over 30-60 minutes and the mixture was stirred for 15-20 minutes at −65±5° C. A solution of ammonium chloride (4.9 kg) in demineralised water (18 L) was mixed with a solution of sodium chloride (3.24 kg) in demineralised water (9 L) and this mixture was added over a period of 1-2 hours to the stirred reaction mass at −65±5° C. and the mixture was then stirred at the same temperature for 15-20 minutes. Cooling was removed and the reaction mass was warmed to 30° C. over 1-2 hours. Demineralised water (36 L) was added to the reaction mass and the pH was adjusted to 6-7 by the addition of a 1:1 mixture of acetic acid and demineralised water at 30° C. The product was extracted into MTBE (2×5 volumes) and the combined extracts were washed with a solution of sodium chloride (13.5 kg) in demineralised water (6 volumes). The solvent was removed from the organic layer under vacuum at <50° C. until approx. 1.5 volumes. This was cooled to 30° C. and a mixture of MTBE (3 volumes) and heptane (2 volumes) was added and the mixture was stirred for 2-3 hours. The solid was collected by filtration and washed with heptane (2 volumes) and then dried under vacuum at 50±5° C. for 6-8 hours to give D1 (12.25 kg).

HPLC retention time for the sample matched that of Description 1 above.

Description 2: (S)-Methyl-5-(4-(benzyloxy)phenyl)-3,4-dihydro-2H-pyrrole-2-carboxylate (D2)

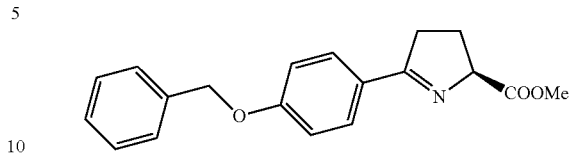

A mixture of (S)-methyl-5-(4-(benzyloxyphenyl)2-((tert-butoxycarbonyl)amino)-5-oxopentanoate (which may be prepared as described herein for Description 1). (35.1 g, 82.1 mmol) in DCM (225 ml) was stirred under nitrogen in an ice bath and trifluoroacetic acid (56 ml, 731.8 mmol) was added over 45 minutes. The mixture was then stirred at room temp for 2 hr. To the mixture cooled in an ice bath was added 26% aqueous potassium bicarbonate solution (approx. 260 ml) to pH 7 (pH meter in aqueous layer, addition took approx. 1 hr). The mixture was then transferred to a separating funnel with more DCM (400 ml) and the layers were separated and the aqueous layer was extracted with another 2×150 ml of DCM. The combined organic layers were washed with water (3×100 ml) and then dried (Na$_2$SO$_4$) and concentrated to give a yellow/brown oil. Heptane (60 ml) was added and the mixture was stirred for a few minutes and scratched with a spatula to give a precipitate. The heptane was decanted off and a further 100 ml of heptane were added and the mixture was stirred for 2 hours at room temperature. The heptane was removed by filtration and the solid was washed with heptane (2×50 ml) and then dried on the filter for a few minutes and then in a vacuum oven at 45° C. to give product as a yellow/brown solid.

NMR indicated a small amount of starting material remained so the isolated product was resubjected to similar reactions conditions and work up to give title compound as a yellow/brown solid (D2), (Yield 22.1 g, 87%)

LC-MS see MH$^+$=310 (C$_{19}$H$_{19}$NO$_3$ requires 309)

NMR (CDCl$_3$): 2.2-2.42 (2H, m), 2.97 (1H, m), 3.15 (1H, m), 3.79 (3H, s), 4.91 (1H, m), 5.13 (2H, s), 7.02 (2H, d, J=9 Hz), 7.30-7.50 (5H, m), 7.86 (2H, d, J=9 Hz).

Description 2: (S)-Methyl-5-(4-(benzyloxy)phenyl)-3,4-dihydro-2H-pyrrole-2-carboxylate (D2) (Alternative Procedure)

A solution of (S)-methyl-5-(4-(benzyloxyphenyl)-2-((tert-butoxycarbonyl)amino)-5-Oxopentanoate (50.00 g, 116.96 mmol), (which may be prepared as described herein for Description 1) in acetonitrile (200 mL) was stirred at 25° C. and methanesulfonic acid (22 mL, 2.9 equivalents, 339.2 mmol) was added dropwise to the reaction mixture whilst maintaining the temperature of <26° C. over a period of 10 minutes. After stirring for 1 hr, the reaction mixture was polish filtered to remove undissolved particles and quenched to a pH of 7.0-8.0 with 4.6 N NH$_4$OH (77 mL) at <25° C. The layers were separated and the aqueous layer was extracted with acetonitrile (50 mL). The combined acetonitrile layers were then heated to >40° C. and water (150 mL) and isopropanol (45 mL) were added, the reaction mixture was then cooled to 22° C. and dry (S)-methyl-5-(4-(benzyloxy)phenyl)-3,4-dihydro-2H-pyrrole-2-carboxylate (D2) seed, 0.5 grams (1%) was added to the reaction mixture. The slurry was aged at 22° C. for 30 minutes then cooled to 15° C. over 30 minutes, aged at 15° C. for 30 minutes, then cooled to −10° C. over 30 minutes. An additional portion of water (200 mL) was added at <0° C. The slurry was filtered and washed with a mixture of room temperature water (75 mL) and isopropanol (22.5 mL). The product was dried to constant weight in vacuo at 50° C. to afford (D2) as a white, crystalline solid. (32.45 g)

Description 2: (S)-Methyl-5-(4-(benzyloxy)phenyl)-3,4-dihydro-2H-pyrrole-2-carboxylate (D2) (Large Scale Plant Manufacture)

A solution of (S)-methyl-5-4-(benzyloxyphenyl)2-((tert-butoxycarbonyl)amino)-5-oxopentanoate (which may be prepared as described herein for Description 1) (21.5 kg) in DCM (6.5 volumes) was stirred at 20-30° C. and trifluoroacetic acid (50.8 kg) was added at such a rate to maintain the temperature at 20-30° C. After completion of the addition, the mixture was stirred at the same temperature for 2-3 hours. The mixture was cooled to 0-10° C. and aqueous potassium bicarbonate solution (2.6M) was added at such a rate to maintain the same temperature until the pH was 7±0.5 (effervescence). The mixture was stirred for 10-15 minutes at 0-10° C. and then warmed to 30-35° C. (all solvent extractions and washings were carried out at 30-35° C.). The layers were separated and the aqueous layer was extracted with more DCM (2.5 volumes) and the combined organic extracts were washed with purified water (10 volumes) and then the organic layer was separated and concentrated under vacuum to approx. 1 volume with respect to starting D1. Heptane (3 volumes) was added and the mixture was concentrated to ~1 volume under vacuum and this process was repeated with another 3 volumes of heptane to chase out residual DCM. To the resulting slurry was added heptane (3 volumes) and the mixture was stirred at 20-25° C. for 2 hours. The solid was collected by filtration, washed with heptane (2 volumes) and then dried under vacuum to afford D2 (13.7 kg).

HPLC retention time for the sample matched that of Description 2 above.

Description 2: (S)-Methyl-5-(4-(benzyloxy)phenyl)-3,4-dihydro-2H-pyrrole-2-carboxylate (D2) (Alternative Large Scale Plant Manufacture)

A mixture of (S)-methyl-5-(4-(benzyloxyphenyl)-2-((tert-butoxycarbonyl)amino)-5-oxopentanoate (115 kg) (which may be prepared as described herein for Description 1) in toluene (637.0 kg) was stirred at 30-35'C until a clear solution forms. Trifluoroacetic acid (271.7 kg) was added to this solution at such a rate to keep the reaction temperature below 35° C. The charge lines were flushed with additional toluene (10 kg) into the reaction vessel. The reaction was stirred for a minimum of 1 hr at 30-35° C. (until <0.5% of starting material remained). After completion of the reaction, the reaction mixture was cooled to 0-10'C and the pH of the solution was adjusted to 7.0±0.5 by the addition of a solution of potassium bicarbonate (275.0 kg) In water (780.0 kg) whilst maintaining the temperature at 0-10° C.—the potassium bicarbonate addition is exothermic and effervescence will occur as carbon dioxide is released during the neutralisation. After neutralisation, the two phase mixture is stirred at 30-35° C. for approximately 15 min. and the 2 layers are then separated. The aqueous layer is stirred at 30-35° C. for approximately 15 min with another lot of toluene (177 kg) and after separation of the layers, the combined toluene extracts were stirred with water (460 kg) at 30-35° C. for approximately 15 min. The separated toluene layer was heated to 40° C. under vacuum until between 800-1000 liters of solvent were removed. Heptane (112.2 kg) was added, maintaining the temperature above 35° C. and the mixture was then cooled to approximately 25° C. to crystallise the product and the mixture was stirred for a minimum of 1 hour at the crystallisation temperature. The mixture was then cooled to 0-5° C. and stirred for a minimum of 1 hour at 0-5° C. and the resulting solid was collected by filtration and washed on the filter with a cooled (0-5° C.) mixture of toluene (25.0 kg) and heptane (39.5 kg). The solid was then dried at up to 40° C. to provide (D2) as white solid (70.8 kg).

Description 3 (2S,5R)-1-tert-Butyl-2-methyl-5-(4-hydroxyphenyl)pyrrolidine-1,2-dicarboxylate (D3)

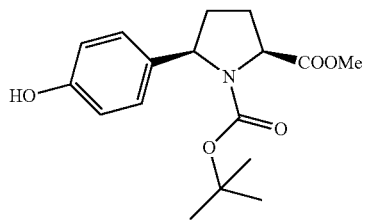 [SMILES: COC(=O)[C@@H]1CC[C@H](c2ccc(O)cc2)N1C(=O)OC(C)(C)C]

A solution of (S)-methyl-5-(4-(benzyloxy)phenyl)-3,4-dihydro-2H-pyrrole-2-carboxylate (which may be prepared as described herein for Description 2) (10.0 g, 32.32 mmol) and Boc$_2$O (7.41 g, 33.94 mmol) in methanol (80 mL) was stirred under nitrogen and 5% Pd—C type 487 paste (1.5 g) was added. The mixture was evacuated under vacuum and filled with N$_2$ (3×) and the flask was then evacuated again and then filled with hydrogen from a balloon and the mixture was stirred overnight under a balloon of hydrogen. After 25 hours, the mixture was evacuated and placed under nitrogen (4×) and then the mixture was filtered under nitrogen through Kieselguhr. The Kieselguhr was washed with methanol (~80 ml) and the filtrate was concentrated and the concentrate was stirred in heptane (30 ml)/ethyl acetate (10 ml) at room temperature for 2 hours. The mixture was then stirred in an ice bath for 10 minutes and filtered. The solid was washed with cold 25% EtOAc in heptane (2×15 ml) and sucked dry on the filter. The solid was then dried in the vacuum oven at 45° C. to give product as a cream solid (D3) (10.39 g, 86%).

LC-MS see MH$^+$=322 (C$_{17}$H$_{23}$NO$_5$ requires 321)

NMR (CDCl$_3$) (mixture of rotamers): 1.19 and 1.43 (9H, 2s), 1.85-2.40 (4H, series of m), 3.83 (3H, s), 4.35-5.50 (3H, series of m), 6.77 (2H, d, J=9 Hz), 7.42 (2H, m).

Description 3 (2S,5R)-1-tert-Butyl-2-methyl-5-(4-hydroxyphenyl)pyrrolidine-1,2-dicarboxylate (D3) (Alternative Procedure)

A 1 L Buchi hydrogenation reactor was charged with 20% Pd(OH)$_2$/C (300 mg, 1 wt %), (S)-methyl-5-(4-(benzyloxy)phenyl)-3,4-dihydro-2H-pyrrole-2-carboxylate (which may be prepared as described herein for Description 2), (30.00 g, 97.0 mmol), di-tert-butyldicarbonate (22.22 g, 102 mmol, 1.05 eq) and methanol (240 mL). The mixture was pressurized with hydrogen gas (4 bar), agitated at ~1000 rpm and maintained at <23° C.; the reaction was sampled periodically for completion (HPLC). Upon completion, Celite® (5 g) was charged to the reactor and stirring was continued for an additional 5-10 min. The mixture was filtered through a pad of Celite® (5 g). The reactor was charged with methanol (200 mL) and this rinse was used to wash the filter cake. The combined filtrate and wash was concentrated by rotary evaporation to low volume and re-concentrated from ethyl acetate (90 mL). Following charging of ethyl acetate (90 mL), heptane (135 mL) was added slowly over about 30 min at ambient temperature with good stirring. After aging for ~2 h at ambient temperature, the slurry was cooled to and aged at 0-5° C. for 1 h, filtered, washed with cold (−5° C.) 1:4 (v/v) ethyl acetate-heptane (2×30 mL) and dried to constant weight in vacuo at 35° C. to afford (D3) as a white, crystalline solid (27.01 g).

Description 3 (2S,5R)-1-tert-Butyl-2-methyl-5-(4-hydroxyphenyl)pyrrolidine-1,2-dicarboxylate (D3) (Alternative Procedure)

A 1 L Buchi hydrogenation reactor was charged with 20% Pd(OH)$_2$/C, (300 mg, 1 wt %), (S)-methyl-5-(4-(benzyloxy)phenyl)-3,4-dihydro-2H-pyrrole-2-carboxylate, (which may be prepared as described herein for Description 2), (30.00 g, 97.0 mmol), N-(tert-butoxycarbonyloxy)succinimide, (21.52 g, 102 mmol, 1.00 eq based on 97% purity) and methanol (360 mL). The mixture was pressurized with hydrogen gas (4 bar), agitated at ~1000 rpm and maintained at <23° C.; the reaction was sampled periodically for completion (HPLC). Upon completion, Celite® (5 g) was charged to the reactor and stirring was continued for an additional 5-10 min. The mixture was filtered through a pad of Celite® (5 g). The reactor was charged with methanol (60 mL) and this rinse was used to wash the filter cake. One-quarter of the combined filtrate and wash was concentrated by rotary evaporation to low volume. Following charging of methanol (15 mL), water (7.5 mL) was added slowly over 15-20 min at ambient temperature with good stirring. After aging for ~35 min at ambient temperature, the slurry was aged at −5° C. overnight, filtered, washed with cold (−5° C.) 1:4 (v/v) methanol-water (2×7.5 mL) and dried to constant weight in vacuo at 35° C. to afford (D3) as a crystalline solid, (6.24 g)

Description 3 (2S,5R)-1-tert-Butyl-2-methyl-5-(4-hydroxyphenyl)pyrrolidine-1,2-dicarboxylate (D3) (Alternative Procedure)

A 1 L Buchi hydrogenation reactor was charged with 20% Pd(OH)$_2$/C (300 mg, 1 wt %), (S)-methyl-5-(4-(benzyloxy)phenyl)-3,4-dihydro-2H-pyrrole-2-carboxylate (which may be prepared as described herein for Description 2), (30.00 g, 97.0 mmol), di-tert-butyldicarbonate (22.41 g, 102 mmol, 1.05 eq corrected for purity) and methanol (360 mL). The mixture was pressurized with hydrogen gas (4 bar), agitated at ~1000 rpm and maintained at <23° C.; the reaction was sampled periodically for completion (HPLC). Upon completion, Celite® (2.5 g) was charged to the reactor and stirring was continued for an additional 5-10 min. The mixture was filtered through a pad of Celite® (2.5 g). The reactor was charged with methanol (60 mL) and this rinse was used to wash the filter cake. One-third of the combined filtrate and wash was concentrated by rotary evaporation at 40° C. and 110 mbar to low volume. Following charging of methanol (20 mL), water (20 mL) was added slowly over about 3 min at ambient temperature with good stirring. After aging about 2 h at ambient temperature, the slurry was aged at −5° C. overnight, filtered, washed with cold (−5° C.) 1:4 (v/v) methanol-water (2×10 mL) and dried to constant weight in vacuo at 35° C. to afford a white, crystalline solid, (D3), (9.51 g).

Description 3 (2S,5R)-1-tert-Butyl-2-methyl-5-(4-hydroxyphenyl)pyrrolidine-1,2-dicarboxylate (D3) (Large Scale Plant Manufacture)

(S)-methyl-5-(4-(benzyloxy)phenyl)-3,4-dihydro-2H-pyrrole-2-carboxylate (which may be prepared as described herein for Description 2) (7.0 kg) and 5% Pd—C(type 487, 0.63 kg) were charged to a hydrogenation vessel under a nitrogen atmosphere. Methanol (9 volumes) and di-tertbutyl dicarbonate (5.18 kg) were added and the charge line was then flushed with a further quantity of methanol (16 kg) to the vessel. The mixture was hydrogenated at 20-30° C. under 4 bar of hydrogen for approx. 30 hours. The reaction contents were filtered under nitrogen to remove catalyst and the filter was washed with more methanol (5 kg). The filtrate was concentrated under vacuum to 15-20 L and ethyl acetate (2.9 volumes) was added and the mixture was concentrated to 2-3 volumes. This was repeated with a further 2.9 volumes of ethyl acetate to chase out the residual methanol. Heptane (4.4 volumes) was added and the mixture was stirred at 20-25° C. for 2 hours and then cooled to 0-4° C. and filtered. The solid product was washed on the filter with 4:1 heptane:ethyl acetate (2×1 volume) and then sucked dry on the filter and dried under vacuum to give product D3 as an off white solid (6.4 kg).

HPLC retention time for the sample matched that of Description 3 above.

Description 4 (2S,5S)-1-ter-Butyl-2-methyl 5-(4-((2-fluorobenzyl)oxy)phenylpyrrolidine-1,2-dicarboxylate (D4)

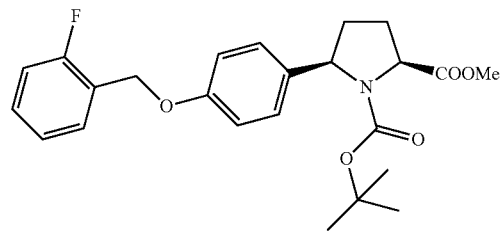 [SMILES: COC(=O)[C@@H]1CC[C@H](c2ccc(OCc3ccccc3F)cc2)N1C(=O)OC(C)(C)C]

Note 2-F BnBr is a severe irritant.

A mixture of (2S,5R)-1-tert-butyl-2-methyl-5-(4-hydroxyphenyl)pyrrolidine-1,2-dicarboxylate (which may be prepared as described herein for Description 3) (7.0 g, 21.78 mmol) and potassium carbonate ((4.52 g, 32.67 mmol) (ground up in a pestle and mortar) was stirred in acetone (60 ml) for 5 minutes at room temperature and then treated with 2-fluorobenzyl bromide (3.42 mL, 28.32 mmol) and the mixture was heated at 55-58° C. for 34 hours. The acetone was evaporated and water and ethyl acetate (150 ml of each) were added and the product was extracted into the ethyl acetate. The water was extracted with more ethyl acetate (100 ml) and the combined extracts were washed with water (100 ml), dried (Na$_2$SO$_4$) and concentrated to give crude D4.

LC-MS see MH$^+$=430 (C$_{24}$H$_{28}$FNO$_5$ requires 429)

Description 4 (2S,5S)-1-tert-Butyl-2-methyl 5-(4-((2-fluorobenzyl)oxy)phenylpyrrolidine-1,2-dicarboxylate (D4) (Alternative Procedure)

A mixture of (2S,5R)-1-tert-butyl-2-methyl-5-(4-hydroxyphenyl)pyrrolidine-1,2-dicarboxylate (which may be prepared as described herein for Description 3) (50 g), powdered potassium carbonate (64.4 g) and tetra n-butyl ammonium bromide (2.5 g) was stirred in ethyl acetate (250 ml) for 10 minutes at room temperature under nitrogen and then treated with 2-fluorobenzyl bromide (30.87 g) and the mixture was heated at 60±5° C. for 4-6 hours. The mixture was cooled to 30° C. and water (250 ml) was added and the product was extracted into the ethyl acetate. The aqueous layer was again extracted with ethyl acetate (150 ml) and the combined organic layers were washed with brine (200 ml) and concentrated under vacuum to 1-1.5 volumes with respect to starting material. Heptane (250 ml) was added and the mixture was warmed until the solids dissolved (up to 50° C.) and stirred for 20 minutes. The solution was then cooled until crystals were observed (~35° C.) and then stirred at this temperature for 1 hr. The mixture was then cooled to ~20° C. over 1 hr and then to 0-5° C. over a further 1 hr and then stirred at 0-5° C. for 3 hrs. The solid was collected by filtration at 0-5° C., washed on the filter with chilled (0-5° C.) heptane (2×100 ml) and then sucked dry on the filter. Drying was completed under vacuum at 40-45° C. to give a white solid (D4), (60.7 g).

Description 4 (2S,5S)-1-tert-Butyl-2-methyl 5-(4-((2-fluorobenzyl)oxy)phenylpyrrolidine-1,2-dicarboxylate (D4) (Large Scale Plant Manufacture)

A reactor was charged with (2S,5R)-1-tert-butyl-2-methyl-5-(4-hydroxyphenyl)pyrrolidine-1,2-dicarboxylate (which may be prepared as described herein for Description 3) (12.0 kg), powdered potassium carbonate (15.5 kg), acetone (10 volumes) and 2-fluorobenzyl bromide (7.75 kg) and the mixture was stirred and refluxed under nitrogen for 30 hours. The mixture was cooled and filtered and the reactor and filter were washed with acetone (5 volumes) and the filtrate was concentrated under vacuum to 20-30 L. Ethyl acetate (4 volumes) was added and the mixture was again concentrated to 20-30 L under vacuum. Ethyl acetate (5 volumes) and water (1.25 volumes) were added and the product was extracted into ethyl acetate. The aqueous layer was extracted again with ethyl acetate (5 volumes) and the combined organic layers were washed with purified water (5 volumes) and then concentrated under vacuum to 20-30 L. Heptane (4 volumes) was added and the mixture was concentrated to 20-30 L under vacuum and this process was repeated with more heptane (4 volumes) to chase out residual ethyl acetate. Heptane/ethyl acetate (50:1, approx. 4.5 volumes) was added and the mixture was heated to 40-44° C. for at least 30 minutes and then the mixture was cooled until crystallisation occurred. The mixture was cooled to 0-4° C. and stirred for 2 hours and the solid was collected by filtration, washed with cold heptane (2 volumes, 2-3 times), sucked dry on the filter and then dried under vacuum to give D4 (14.1 kg).

HPLC retention time for the sample matched that of Description 4 above.

Description 5: (2S,5R)-Methyl-5-(4-((2-fluorobenzyl)oxy)phenyl)pyrrolidine-2-carboxylate (D5)

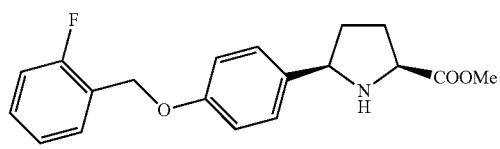 [SMILES: COC(=O)[C@@H]1CC[C@H](c2ccc(OCc3ccccc3F)cc2)N1]

The crude (2S,5S)-1-tert-Butyl-2-methyl 5-(4-((2-fluorobenzyl)oxy)phenylpyrrolidine-1,2-dicarboxylate obtained in the first Description 4 above was stirred in 4M HCl in dioxan (60 ml) for 2 hours and then the solvent was evaporated to give a gum. It is essential to remove excess 2-F Bn Br to avoid it reacting in subsequent steps. Re-evaporation of the gummy product from ethyl acetate gave a foam, this was swirled first with diethyl ether (100 ml) and decanted and then stirred in 1:1 ethyl acetate/isohexane (100 ml) and decanted. The foam was dried, re-suspended in diethyl ether (100 ml) and stirred for 1 hour and the diethyl ether was decanted and the pinkish solid was dried under vacuum. This solid was partitioned between ethyl acetate and 10% sodium carbonate solution (150 ml of each) and the product was extracted into ethyl acetate (this 150 ml and another 150 ml). The combined extracts were washed with water (100 ml) and then dried ($Na_2SO_4$) and concentrated. Methanol (50 ml) was added and the solution re-evaporated to give product as an orange oil (D5)(6.40 g, 89%)

LC-MS see $MH^+$=330 ($C_{19}H_{20}FNO_3$ requires 329)

NMR ($CDCl_3$): 1.72 (1H, m), 2.10-2.30 (4H, series of m), 3.79 (3H, s), 3.94 (1H, m), 4.18 (1H, m), 5.15 (2H, s), 6.98 (2H, d, J=9 Hz), 7.10 (1H, m), 7.18 (1H, m), 7.32 (1H, m), 7.39 (2H, d, J=9 Hz), 7.52 (1H, m).

Description 5: (2S,5R)-Methyl-5-(4-((2-fluorobenzyl)oxy)phenyl)pyrrolidine-2-carboxylate (D5) (Large Scale Plant Manufacture)

A solution of (2S,5S)-1-tert-Butyl-2-methyl 5-(4-((2-fluorobenzyl)oxy)phenylpyrrolidine-1,2-dicarboxylate (which may be prepared as described herein for Description 4) (14 kg) in MTBE (3 volumes) was cooled to 0-5° C. and treated with 81.5% phosphoric acid (89.6 kg) whilst maintaining the temperature at 0-10° C. with external cooling. After completion of the addition, the mixture was stirred at 15-20° C. for approx. 6 hours. The mixture was cooled to 0-10° C. and MTBE (7 volumes) was added.

In a separate flask a solution of ammonium carbonate solution (42 kg in 12 volumes of water) and 33.5% aqueous ammonia (4 volumes) was stirred at 0-10° C. under nitrogen and to this was added the reaction mass above whilst maintaining the temperature below 35° C. with external cooling. The pH of the aqueous was checked to ensure it was in the range 7.5-9.0 (this can be adjusted if necessary by the addition of either phosphoric acid or ammonia solution). The layers were separated (product is in the organic layer) and the aqueous layer was extracted with more MTBE (2×2 volumes) and the organic extracts were combined and washed with sodium carbonate solution (7 kg in 10 volumes of water) and then water (10 volumes). The organic solution was concentrated to 15-20 L and MTBE (2 volumes) was added and this solution of D5 was stored at 2-8° C. under nitrogen. (Estimated yield 10.4 kg)

HPLC retention time for the sample matched that of Description 5 above.

Description 5a: (2S,5R)-Methyl-5-(4-((2-fluorobenzyl)oxy)phenyl)pyrrolidine-2-carboxylate p-toluenesulfonate salt (D5a) (Large Scale Plant Manufacture)

(2S,5S)-1-tert-Butyl-2-methyl 5-(4-((2-fluorobenzyl)oxy) phenylpyrrolidine-1,2-dicarboxylate (which may be prepared as described herein for Description 4) (83.5 kg) and para-toluenesulfonic acid (45.8 kg) were charged to a reactor and methanol (263.8 kg) was added and the reaction temperature was adjusted to 45-55° C. and stirred at this temperature for 2-3 hours. When reaction was judged to be complete (<1% of starting material remains), the temperature was adjusted to 35-40° C. and MTBE (859.2 kg) was added whilst maintaining the temperature at 35-40° C. The mixture was then stirred at 30-40° C. for approximately 30 minutes and then cooled to 0±5° C. and then stirred at this temperature for approximately 1 hour. The resulting solid was collected by filtration and washed on the filter with cooled (to 0-5'C) MTBE (184.2 kg) and then dried at 30-40° C. to give (D5a), (89.8 kg).

Description 6: (2S,5R)-5-(4-((2-Fluorobenzyl)oxy) phenyl)pyrrolidine-2-carboxamide (D6)

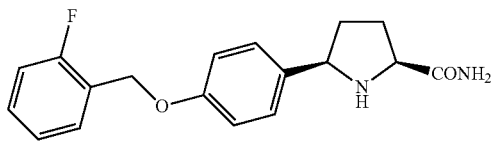 [SMILES: NC(=O)[C@@H]1CC[C@H](c2ccc(OCc3ccccc3F)cc2)N1]

A mixture of (2S,5R)-methyl 5-(4-((2-fluorobenzyl)oxy) phenyl)pyrrolidine-2-carboxylate (which may be prepared as described herein for Description 5) (6.4 g, 19.43 mmol) in 7M ammonia in methanol (52.47 mL, 367.27 mmol) was stirred in a sealed flask. After leaving to stand for 4 days, the solvent was evaporated and toluene (12 ml) was added and re-evaporated. The resulting solid was stirred in toluene (10.5 ml) for 2 hours and then heptane (3.5 ml) was added and the mixture was stirred for a further 30 minutes at room temperature and then in an ice-bath for 30 minutes. The solid was collected by filtration and washed with cold 3:1 toluene/heptane (12 ml) and then with heptane (12 ml) and sucked dry. Drying was completed in the vacuum oven at 45° C. to give product as a beige solid (5.85 g). NMR showed a trace impurity in aromatic region (6.8-6.9 ppm). It was thought this could be some unreacted phenol from an earlier step, therefore the material was taken up in ethyl acetate (200 ml) and washed with 2% $Na_2CO_3$ solution (2×100 ml) and water (100 ml) and then dried over $Na_2SO_4$ and concentrated to give product as an off white powder (D6), (5.47 g, 90%).

LC-MS MH+=315 ($C_{18}H_{19}FN_2O_2$)

NMR ($CDCl_3$): 1.68 (1H, m), 2.06-2.35 (3H, series of m), 2.51 (1H, br s), 3.88 (1H, dd, J=3 Hz, 9 Hz), 4.31 (1H, dd, J=6 Hz, 9 Hz), 5.15 (2H, s), 5.57 (1H, br s), 6.99 (2H, d, J=9 Hz), 7.11 (1H, m), 7.18 (1H, m), 7.30-7.40 (3H, m), 7.53 (1H, m).

Description 6: (2S,5R)-5-(4-((2-Fluorobenzyl)oxy) phenyl)pyrrolidine-2-carboxamide (06) (Large Scale Plant Manufacture)

The solution of (2S,5R)-methyl 5-(4-((2-fluorobenzyl) oxy)phenyl)pyrrolidine-2-carboxylate obtained in Description 5 (Large Scale Plant Manufacture) above was placed in a reactor and concentrated below 40° C. under vacuum to approx. 15 L. Methanol (2 volumes) was added and the solution was again concentrated to approx. 15 L A solution of $NH_3$ in methanol, (6-7M, 115 kg) was added and the mixture was stirred in a sealed vessel at 25-30° C. for 30 hours. The reaction was concentrated to below 2 volumes below 50° C. and toluene (3 volumes) was added and the mixture again concentrated below to 2 volumes. More toluene (3 volumes) was added and the mixture again concentrated to below 2 volumes to remove residual methanol. Toluene (3 volumes) was added and the mixture was heated at 40-50° C. for 30 minutes and heptane (1 volume) was added at the same temperature. The mixture was cooled to 25-35° C. and stirred for 2-3 hours and then further cooled to 0-5° C. and stirred for 2-3 hours. The solid was collected by filtration and washed with chilled heptane (2 volumes)/toluene (0.5 volumes) and then sucked dry for 1-2 hours. The solid was stirred with purified water (5 volumes) at 25-35° C. for 1-2 hours and collected by filtration and washed with purified water (2 volume batches) until the pH of the aqueous filtrate was 5-7.5. The solid was sucked dry for 1-2 hours and then washed with heptane (2 volumes) and then dried under vacuum to give D6 (9.2 kg) HPLC retention time for the sample matched that of Description 6 above.

Description 6: (2S,5R)-5-(4-((2-Fluorobenzyl)oxy) phenyl)pyrrolidine-2-carboxamide (D6) (Alternative Large Scale Plant Manufacture)

(2S,5R)-Methyl-5-(4-((2-fluorobenzyl)oxy)phenyl)pyrrolidine-2-carboxylate p-toluenesulfonate salt (which may be prepared as described herein for Description 5a) (80.0 kg) was charged to a reactor and the reactor was purged with nitrogen. MTBE (296 kg) and water (76.4 kg) were added followed by 33% aqueous ammonia solution (63.4 kg). The reaction was stirred for 15 minutes at 25-35° C. and the mixture was then allowed to settle for 15 minutes and the lower aqueous layer was removed. The MTBE solution was stirred with sodium carbonate solution (440 kg of a solution of 80 kg of sodium carbonate in 800 kg of water) for 15 minutes and then the mixture was allowed to settle for 15 minutes and the lower aqueous layer was removed. The MTBE solution was then washed with water (240 kg) and brine (260 kg) and then placed under vacuum at 40° C. and 200-300 kg of the MTBE were evaporated. Methanol (63 kg) was added and the mixture was again distilled under vacuum at 40° C. until 40-80 kg of distillate had been collected. The reaction mixture was then cooled to below 20° C. and 7N ammonia in methanol (312 kg) was added whilst maintaining the temperature below 30° C. The temperature was then adjusted to 25-30° C. and the mixture was stirred for 24 hrs. A further charge of ammonia solution may be necessary if the reaction has not reached completion. Purified water (400 kg) was added to the mixture whilst maintaining the temperature at 25-30° C. and then the mixture was stirred for 1-2 hrs at 25-30° C. The resulting suspension was filtered and the solid was washed on the filter with a mixture of purified water (80 kg) and methanol (63 kg). The solid was dried under vacuum at <50° C. to give product as a white solid (D6)(47 kg). The product can be recrystallized using methanol (8.5 volumes)/purified water (8.5 volumes) if required.

Example 1: (2S,5R)-5-(4-((2-Fluorobenzyl)oxy) phenyl)pyrrolidine-2-carboxamide hydrochloride (E1)

A solution of (2S,5R)-5-(4-((2-fluorobenzyl)oxy)phenyl) pyrrolidine-2-carboxamide (which may be prepared as described herein for Description 6) (5.46 g, 17.37 mmol) in ethyl acetate (140 mL) was stirred for 30 minutes and filtered. The filtrate was treated with 4M HCl in dioxan (6.51 mL, 26.05 mmol) and the mixture was stirred at room temperature for 20 minutes and then cooled in an ice bath for 15 minutes. The resulting solid was collected by filtration and washed with cold ethyl acetate (2×20 ml) and then dried under vacuum at 35° C. overnight, then at 50° C. for 2 hours to give product as an off white solid (E1), (5.87 g, 96%).

LC-MS MH+=315 ($C_{18}H_{19}FN_2O_2$)

NMR (d6-DMSO): 1.95-2.20 (2H, m), 2.30 (2H, m), 3.35 (1H, s), 4.30 (1H, m), 4.61 (1H, m), 5.18 (2H, s), 7.10 (2H, d, J=9 Hz), 7.18-7.30 (2H, m), 7.40 (1H, m), 7.47 (2H, d, J=9 Hz), 7.56 (1H,), 7.72 (1H, s), 8.07 (1H, s), 10.60 (1H, br s).

Example 1: (2S,5R)-5-(4-((2-Fluorobenzyl)oxy)phenyl)pyrrolidine-2-carboxamide hydrochloride (E1) (Alternative Procedure)

A solution of (2S,5R)-5-(4-((2-fluorobenzyl)oxy)phenyl)pyrrolidine-2-carboxamide (which may be prepared as described herein for Description 6) (15.0 g, 47.8 mmol) in ethanol (17 volumes) was stirred at 30±5° C. for 30-45 minutes and filtered and the filter was washed with ethanol (1 volume). The filtrate was cooled to 20-25° C. and ethanolic HCl (1.2N, 4.15 volumes) was added over a period of 30-60 minutes at 20-25° C. The mixture was then stirred at 30±5° C. for 2-3 hours and then at 0-5° C. for 2-3 hours. The solid was collected by filtration and washed on the filter with chilled (0-5° C.) ethanol (4 volumes) and then sucked dry on the filter. The solid was dried under vacuum up to 60-70° C. to give product E1 as a white solid (15.5 g).

Example 1: (2S,5R)-5-(4-((2-Fluorobenzyl)oxy)phenyl)pyrrolidine-2-carboxamide hydrochloride (E1) (Large Scale Plant Manufacture)

A solution (2S,5R)-5-(4-((2-Fluorobenzyl)oxy)phenyl)pyrrolidine-2-carboxamide (9.0 kg) (which may be prepared as described herein for Description 6) in ethanol (96.0 kg, Doubly Rectified Absolute Alcohol) is heated to a maximum of 50° C. to dissolve. The temperature was adjusted to 30-40° C. and the solution was filtered and flushed with more ethanol (31 kg). A solution of 1.25M hydrogen chloride in ethanol (31 kg) was added over a minimum of 30 min, maintaining the temperature between 20-25'C. Note: This addition was exothermic and cooling was required. The hydrogen chloride solution was rinsed in with more ethanol (3 kg) and the mixture was stirred at 25-35° C. for approximately 2 hours. The temperature was adjusted to 0-5° C. and the mixture was stirred for approximately 2 hours. The solid was collected by filtration and washed with chilled ethanol (2×14 kg). The wet cake was dried under vacuum up to 70° C. to give product as a white solid (E1)(9.6 kg).

What is claimed is:

1. A compound of formula (I):

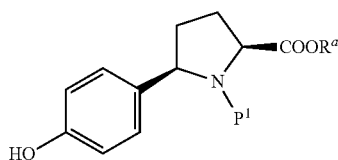

(I)

wherein $R^a$ is $C_{1-3}$ alkyl, and $P^1$ is an amine protecting group selected from the group consisting of tert-butyloxycarbonyl (BOC); 9-fluorenylmethyloxycarbonyl (FMOC); acetyl (Ac); benzoyl (Bz); carbamate; p-methoxyphenyl (PMP); tosyl (Ts); Nosyl; Nps and trifluoroacetyl.

2. The compound of formula (I) according to claim 1, wherein $P^1$ is tert-butyloxycarbonyl (BOC).

3. The compound of formula (I) according to claim 2, wherein the compound is a compound of formula (I)$^c$:

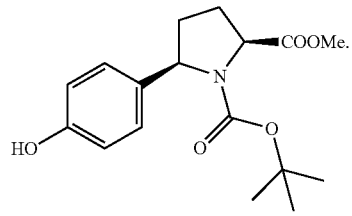

(I)$^c$

4. A process for preparing a compound of formula (I)

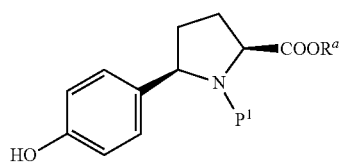

(I)

comprising the steps of:

(i) preparing a compound of formula (II) by reacting a compound of formula (III) with a compound of formula (IV):

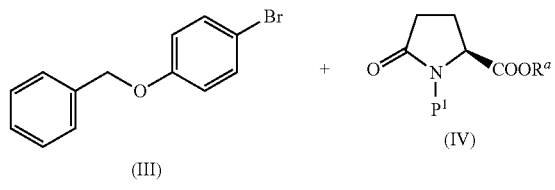

|Step (a)

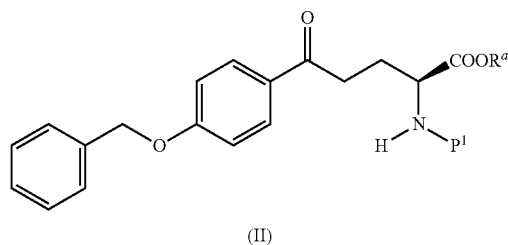

(II)

wherein $R^a$ is $C_{1-3}$ alkyl and $P^1$ is an amine protecting group selected from the group consisting of tert-butyloxycarbonyl (BOC); 9-fluorenylmethyloxycarbonyl (FMOC); acetyl (Ac); benzoyl (Bz); carbamate; p-methoxyphenyl (PMP); tosyl (Ts); Nosyl; Nps and trifluoroacetyl;

(ii) preparing a compound of formula (V) from a compound of formula (II):

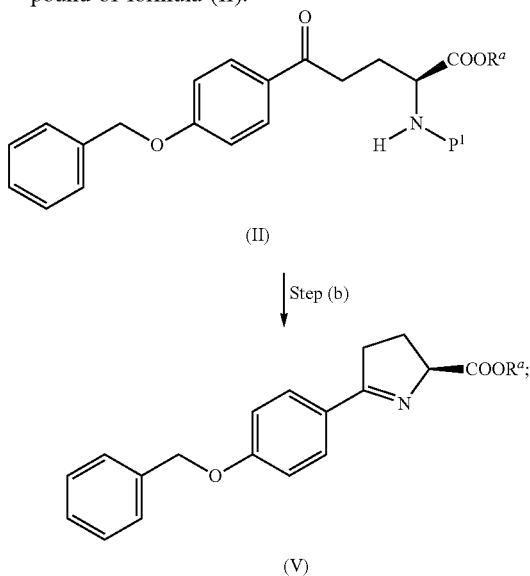

(II)

Step (b)

(V)

and (iii) preparing a compound of formula (I) from a compound of formula (V):

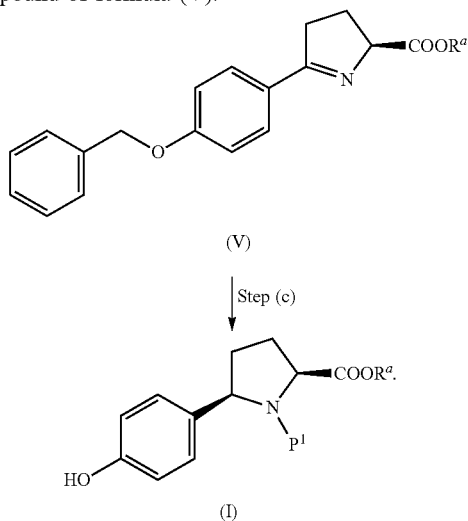

(V)

Step (c)

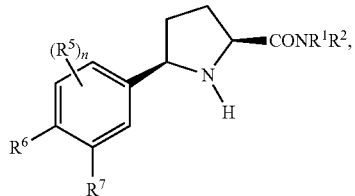

(I)

5. The process according to claim 4, wherein step (a) comprises the use of magnesium and a solvent, and step (b) comprises the use of a solvent and an acid.

6. The process according to claim 4, wherein $P^1$ is tert-butyloxycarbonyl (BOC), and step (c) comprises the use of $Boc_2O$ in a solvent and in the presence of a catalyst.

7. A process of preparing a compound of formula (VI)

(VI)

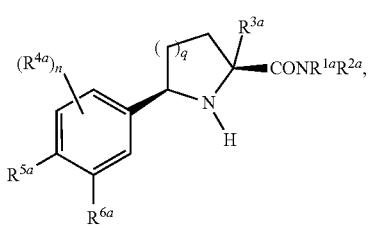

comprising using a compound of formula (I)

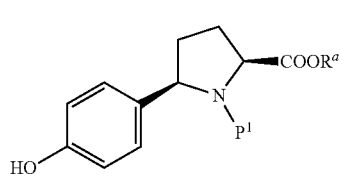

(I)

as an intermediate;
wherein
$R^1$ and $R^2$ are independently hydrogen, $C_{1-6}$ alkyl or $C_{3-6}$ cycloalkyl$C_{1-6}$ alkyl; or such $R^1$ and $R^2$, together with the nitrogen to which they are attached, may form an unsubstituted 3-, 4-, 5- or 6-membered saturated ring;
n is 0;
$R^6$ is —O—$R^8$ or —OCHR$^9$R$^8$;
$R^7$ is hydrogen;
$R^8$ is a phenyl ring optionally substituted by one or more groups independently selected from the list consisting of $C_{1-3}$ alkyl, halogen, cyano, halo$C_{1-3}$ alkyl, hydroxy, $C_{1-3}$ alkoxy and $C_{1-3}$ haloalkoxy; and
$R^9$ is hydrogen or $C_{1-3}$ alkyl.

8. The process as defined in claim 7, wherein the compound of formula (VI) is a compound of formula (VI)$^a$:

(VI)$^a$

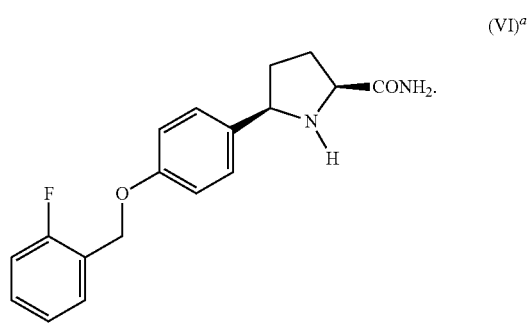 [SMILES: NC(=O)[C@@H]1CC[C@H](c2ccc(OCc3ccccc3F)cc2)N1]

9. A process of preparing a compound of formula (X)

(X)

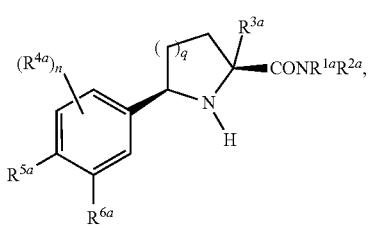

comprising using a compound of formula (I)

(I)

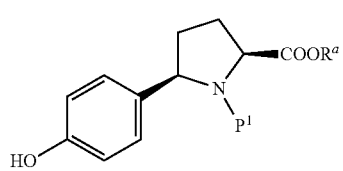

as an intermediate;

wherein

R¹ᵃ and R²ᵃ are independently hydrogen, $C_{1-6}$ alkyl or $C_{3-6}$ cycloalkyl$C_{1-6}$ alkyl; or such R¹ᵃ and R²ᵃ, together with the nitrogen to which they are attached, may form an unsubstituted 3-, 4-, 5- or 6-membered saturated ring;

R³ᵃ is $C_{1-6}$ alkyl, $C_{1-6}$ haloalkyl, $C_{1-3}$ alkenyl, $C_{1-3}$ alkoxy$C_{1-3}$ alkyl, $C_{1-3}$ haloalkoxy$C_{1-3}$ alkyl or $(CH_2)_tOH$;

or such R¹ᵃ and R³ᵃ, together with the interconnecting atoms, form a saturated or unsaturated 5- to 7-membered ring, with the proviso that there is only one heteroatom in the ring, which must be nitrogen;

n is 0;

q is 1 or 2;

t is 1 or 2;

R⁵ᵃ is —O—R⁷ᵃ or —OCH₂R⁷ᵃ;

R⁶ᵃ is hydrogen;

R⁷ᵃ is either a phenyl ring or a 5- or 6-membered aromatic heterocyclic ring (independently containing one or more nitrogen, sulphur or oxygen atoms) wherein either the phenyl ring or the heterocyclic ring is optionally substituted by one or more groups independently selected from the list consisting of $C_{1-3}$ alkyl, halogen, cyano, halo$C_{1-3}$ alkyl, hydroxy, $C_{1-3}$ alkoxy and $C_{1-3}$ haloalkoxy.

10. The process as defined in claim 9, wherein the compound of formula (X) is a compound of formula (X)ᵇ:

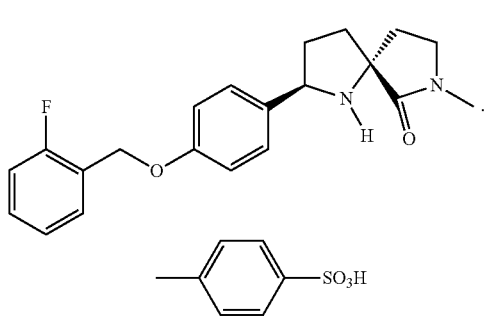

(X)ᵇ

11. A process for preparing a compound of formula (VI)ᵃ

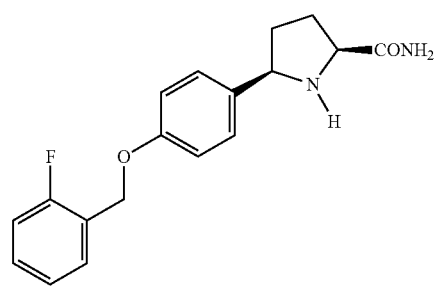

(VI)ᵃ comprising the steps of:
(i) preparing a compound of formula (VII) from a compound of formula (I) by reacting the compound of formula (I) with a compound of formula (VIII):

(I) + (VIII) →(Step (d)) (VII)

wherein Rᵃ is $C_{1-3}$ alkyl, P¹ is an amine protecting group selected from the group consisting of tert-butyloxycarbonyl (BOC); 9-fluorenylmethyloxycarbonyl (FMOC); acetyl (Ac); benzoyl (Bz); carbamate; p-methoxyphenyl (PMP); tosyl (Ts); Nosyl; Nps and trifluoroacetyl; and L¹ is a leaving group;

(ii) preparing a compound of formula (IX) from a compound of formula (VII) by removal of the P¹ group under deprotection conditions:

(VII) →(Step (e)) (IX)

and (iii) preparing a compound of formula (VI)$^a$ from a compound of formula (IX):

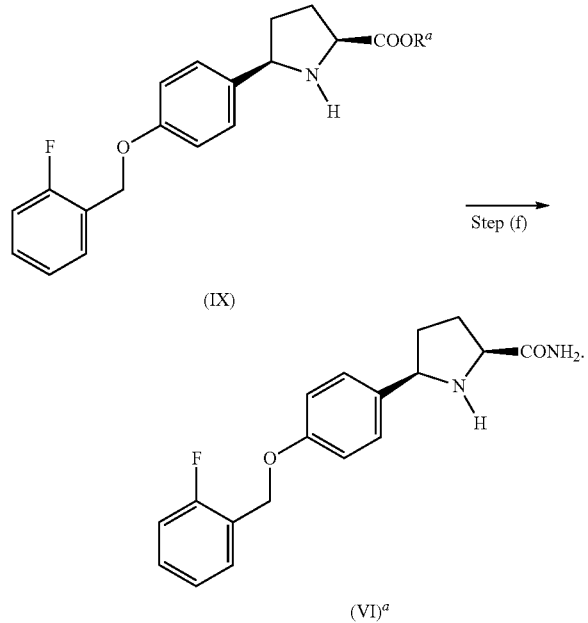

(IX)

(VI)$^a$

12. The process of claim 11, wherein L$^1$ is a halogen.

13. The process of claim 11, wherein step (d) comprises the use of a base and a solvent.

14. The process of claim 11, wherein P$^1$ is tert-butyloxycarbonyl (BOC) and step (e) comprises the use of a strong acid in a solvent.

15. The process of claim 11, wherein step (f) comprises the use of ammonia in a solvent.

16. The process of claim 11, additionally comprising the step of preparing a salt of a compound of formula (VI)$^a$ by treating the compound of formula (VI)$^a$ with an acid.

17. The process of claim 16, wherein the salt of a compound of formula (VI)$^a$ is a hydrochloride salt.

18. A process for preparing a compound of formula (VI)$^a$:

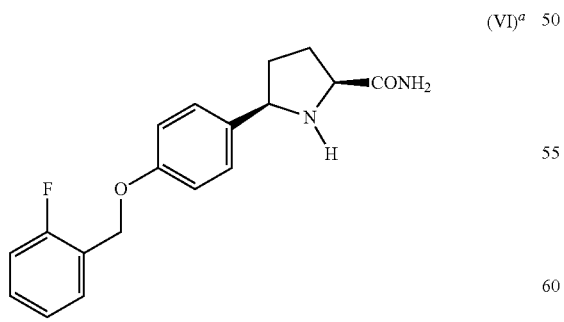

(VI)$^a$ comprising the steps of:

(i) preparing a compound of formula (II) by reacting a compound of formula (III) with a compound of formula (IV):

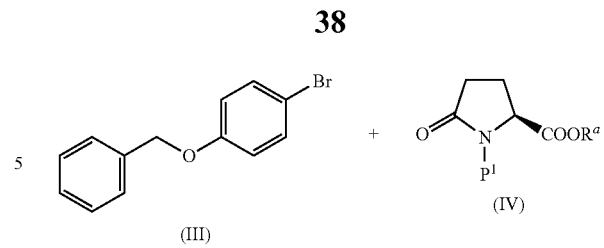

(III)

(IV)

wherein R$^a$ is C$_{1-3}$ alkyl and P$^1$ is a protecting group;

(ii) preparing a compound of formula (V) from a compound of formula (II):

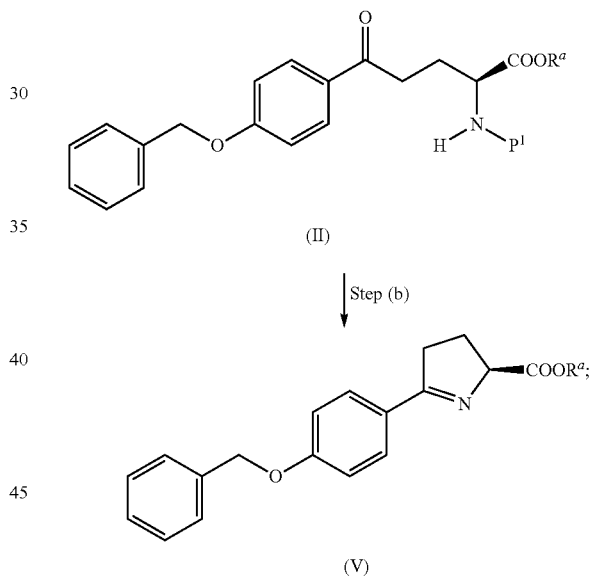

(II)

(V)

(iii) preparing a compound of formula (I) from a compound of formula (V):

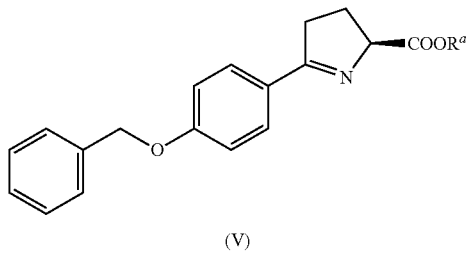

(V)

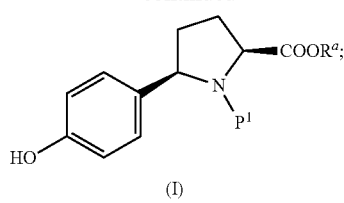

(iv) preparing a compound of formula (VII) from a compound of formula (I) by reacting the compound of formula (I) with a compound of formula (VIII):

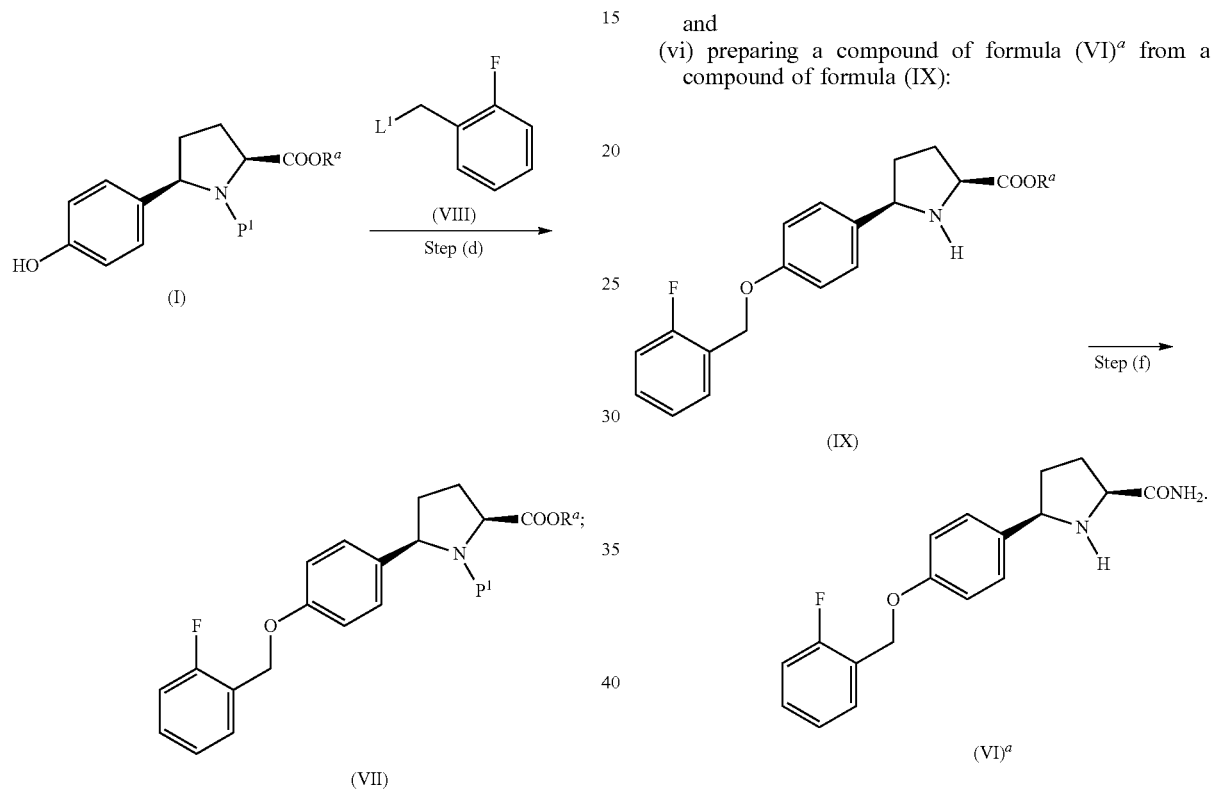

(v) preparing a compound of formula (IX) from a compound of formula (VII) by removal of the P¹ group under deprotection conditions:

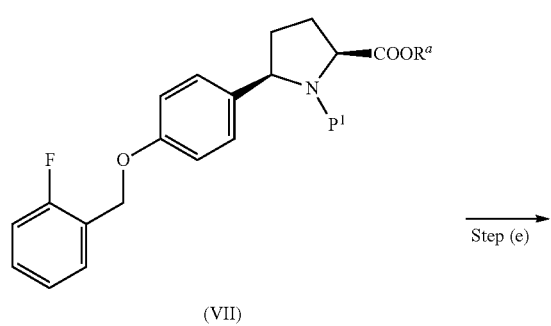

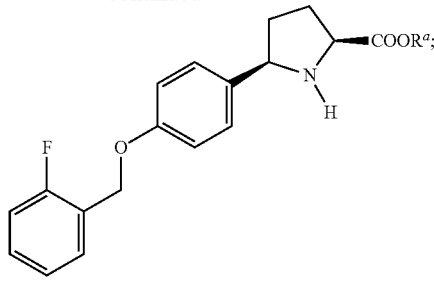

and (vi) preparing a compound of formula (VI)$^a$ from a compound of formula (IX):

19. The process according to claim 18, wherein step (a) comprises the use of magnesium and a solvent, and step (b) comprises the use of a solvent and an acid.

20. The process according to claim 18, wherein P¹ is tert-butyloxycarbonyl (BOC), and step (c) comprises the use of Boc$_2$O in a solvent and in the presence of a catalyst.

21. The process of claim 18, wherein L¹ is a halogen.

22. The process of claim 18, wherein step (d) comprises the use of a base and a solvent.

23. The process of claim 18, wherein P¹ is tert-butyloxycarbonyl (BOC) and step (e) comprises the use of a strong acid in a solvent.

24. The process of claim 18, wherein step (f) comprises the use of ammonia in a solvent.

25. The process of claim 18, additionally comprising the step of preparing a salt of a compound of formula (VI)$^a$ by treating the compound of formula (VI)$^a$ with an acid.

26. The process of claim 25, wherein the salt of a compound of formula (VI)$^a$ is a hydrochloride salt.

* * * * *